United States Patent
Saul et al.

(10) Patent No.: US 9,980,786 B2
(45) Date of Patent: May 29, 2018

(54) MEDICAL DEVICES AND METHODS OF USE

(71) Applicants: Tom Saul, Moss Beach, CA (US); Amr Salahieh, Saratoga, CA (US); Alan Schaer, San Jose, CA (US)

(72) Inventors: Tom Saul, Moss Beach, CA (US); Amr Salahieh, Saratoga, CA (US); Alan Schaer, San Jose, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 0 days. days.

(21) Appl. No.: 15/833,330

(22) Filed: Dec. 6, 2017

(65) Prior Publication Data
US 2018/0098821 A1  Apr. 12, 2018

Related U.S. Application Data

(63) Continuation of application No. PCT/US2017/042859, filed on Jul. 19, 2017.

(60) Provisional application No. 62/364,268, filed on Jul. 19, 2016, provisional application No. 62/404,711, filed on Oct. 5, 2016.

(51) Int. Cl.
*A61B 8/12* (2006.01)
*A61B 90/70* (2016.01)
*A61B 8/00* (2006.01)

(52) U.S. Cl.
CPC .............. *A61B 90/70* (2016.02); *A61B 8/12* (2013.01); *A61B 8/445* (2013.01); *A61B 8/4411* (2013.01); *A61B 2090/701* (2016.02); *Y10T 29/4913* (2015.01)

(58) Field of Classification Search
CPC ...... H01R 9/001; H01R 12/61; H01R 43/205; Y10T 29/49005; Y10T 29/4908; Y10T 29/49174; A61B 8/12; A61B 8/44; A61B 8/4411; A61B 8/4422; A61B 8/445; A61B 90/70; A61B 2090/701; A61L 2202/24
See application file for complete search history.

(56) References Cited

U.S. PATENT DOCUMENTS

| | | | |
|---|---|---|---|
| 4,802,487 | A | 2/1989 | Martin et al. |
| 5,817,015 | A | 10/1998 | Adair |
| 5,954,654 | A | 9/1999 | Eaton et al. |
| 6,100,626 | A | 8/2000 | Frey et al. |
| 6,537,217 | B1 | 3/2003 | Bjærum et al. |
| 6,559,389 | B1 | 5/2003 | Kornrumpf et al. |
| 6,669,690 | B1 | 12/2003 | Okada et al. |

(Continued)

OTHER PUBLICATIONS

Wildes et al.; 4D ICE: A 2D Array transducer with integrated ASIC in a 10 Fr catheter for real-time 3D intracardiac echocardiography; IEEE Tansactions on ultrasonics, ferroelectrics, and frequency control; 63 (12); pp. 2159-2173;15 pages; (Author Manuscript); Dec. 2016.

*Primary Examiner* — Peter DungBa Vo
*Assistant Examiner* — Joshua D Anderson
(74) *Attorney, Agent, or Firm* — Shay Glenn LLP

(57) ABSTRACT

Systems, and methods of disassembling systems that includes a medical device, a shaft that is optionally steerable, and a handle assembly. The methods can include providing a system after it has been exposed to a blood environment of a subject, disconnecting a medical device electrical contact from an electrical contact on the printed circuit board, moving the medical distally relative to the sheath and out of the distal end of the sheath, and cleaning at least a portion of the medical device.

4 Claims, 14 Drawing Sheets

(56) References Cited

U.S. PATENT DOCUMENTS

| | | |
|---|---|---|
| 7,257,051 B2 | 8/2007 | Thomenius et al. |
| 7,297,118 B2 | 11/2007 | Kristoffersen |
| 7,331,927 B2 | 2/2008 | Steen |
| 7,338,450 B2 | 3/2008 | Kristoffersen et al. |
| 7,451,650 B2 | 11/2008 | Halvorsrod et al. |
| 7,507,205 B2 | 3/2009 | Borovsky et al. |
| 7,527,591 B2 | 5/2009 | Haugen et al. |
| 7,527,592 B2 | 5/2009 | Haugen et al. |
| 7,569,015 B2 | 8/2009 | Donaldson et al. |
| 7,621,028 B2 | 11/2009 | Gelly et al. |
| 7,691,095 B2 | 4/2010 | Bednarek et al. |
| 7,731,516 B2 | 6/2010 | Puttinger et al. |
| 7,740,584 B2 | 6/2010 | Donaldson et al. |
| 7,766,833 B2 | 8/2010 | Lee et al. |
| 7,783,339 B2 | 8/2010 | Lee et al. |
| 7,791,252 B2 | 9/2010 | Baumgartner et al. |
| 7,819,802 B2 | 10/2010 | Secora |
| 7,824,335 B2 | 11/2010 | Wodnicki |
| 7,966,058 B2 | 6/2011 | Xue et al. |
| 8,057,397 B2 | 11/2011 | Li et al. |
| 8,096,951 B2 | 1/2012 | Kristoffersen et al. |
| 8,207,652 B2 | 6/2012 | Baumgartner et al. |
| 8,213,693 B1 | 7/2012 | Li |
| 8,364,242 B2 | 1/2013 | Li |
| 8,428,690 B2 | 4/2013 | Li et al. |
| 8,451,155 B2 | 5/2013 | Amemiya et al. |
| 8,527,032 B2 | 9/2013 | Li |
| 8,659,212 B2 | 2/2014 | Eggen et al. |
| 8,721,553 B2 | 5/2014 | Lee et al. |
| 8,727,993 B2 | 5/2014 | Lee et al. |
| 8,742,646 B2 | 6/2014 | Wodnicki et al. |
| 8,776,335 B2 | 7/2014 | Baumgartner |
| 8,790,262 B2 | 7/2014 | Li et al. |
| 8,840,560 B2 | 9/2014 | Hossack et al. |
| 8,848,560 B2 | 9/2014 | Muruganathan et al. |
| 8,933,613 B2 | 1/2015 | Amemiya et al. |
| 8,978,216 B2 | 3/2015 | Calisti et al. |
| 8,989,842 B2 | 3/2015 | Li et al. |
| 9,055,883 B2 | 6/2015 | Tgavalekos et al. |
| 9,295,511 B2 | 3/2016 | Smith et al. |
| 9,439,625 B2 | 9/2016 | Cogan et al. |
| 9,575,165 B2 | 2/2017 | Miller et al. |
| 9,639,056 B2 | 5/2017 | Falter et al. |
| 2008/0287783 A1 | 11/2008 | Anderson |
| 2010/0113942 A1 | 5/2010 | Eberle |
| 2010/0249598 A1 | 9/2010 | Smith et al. |
| 2011/0087071 A1 | 4/2011 | Danitz et al. |

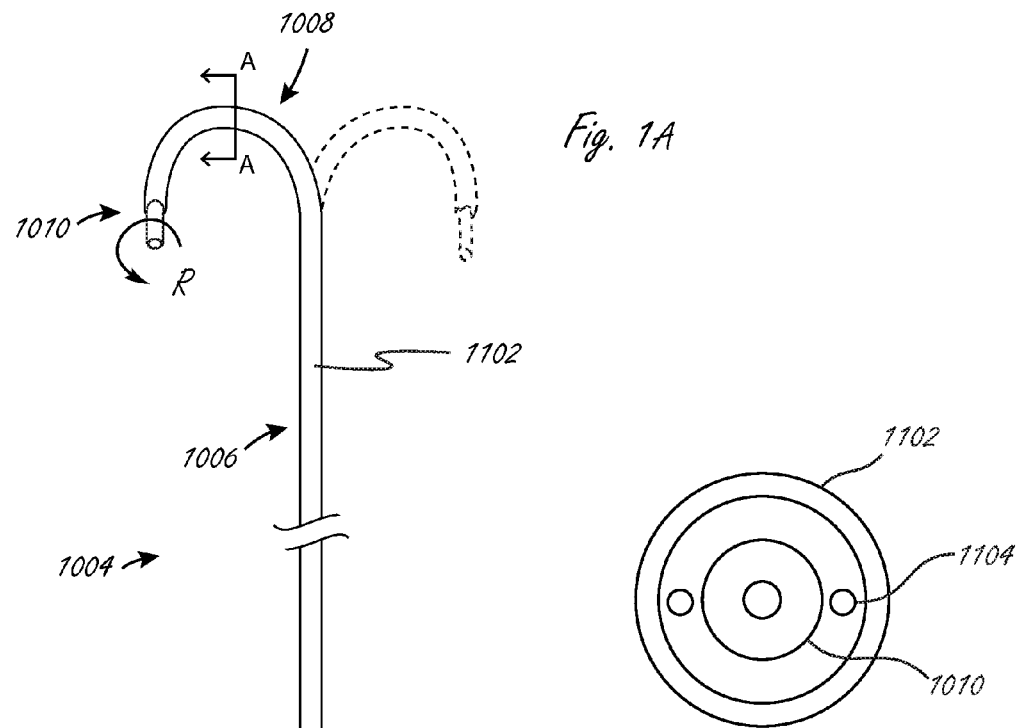
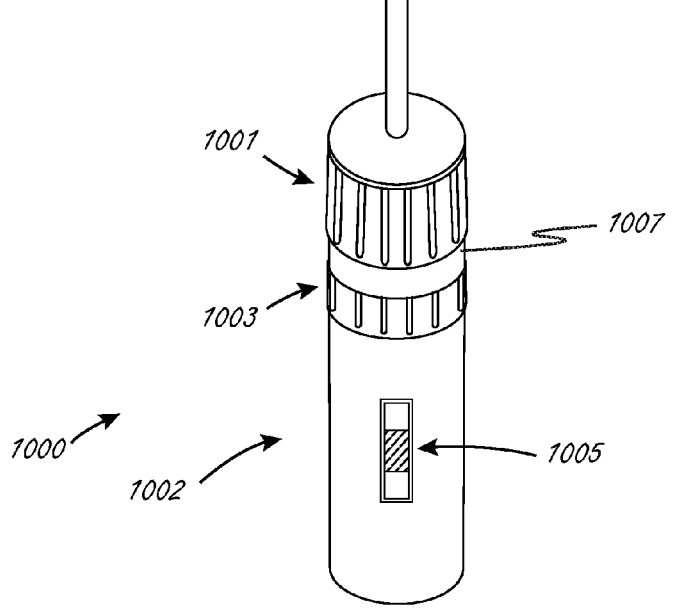
SECTION A-A
Fig. 1B
Fig. 1A

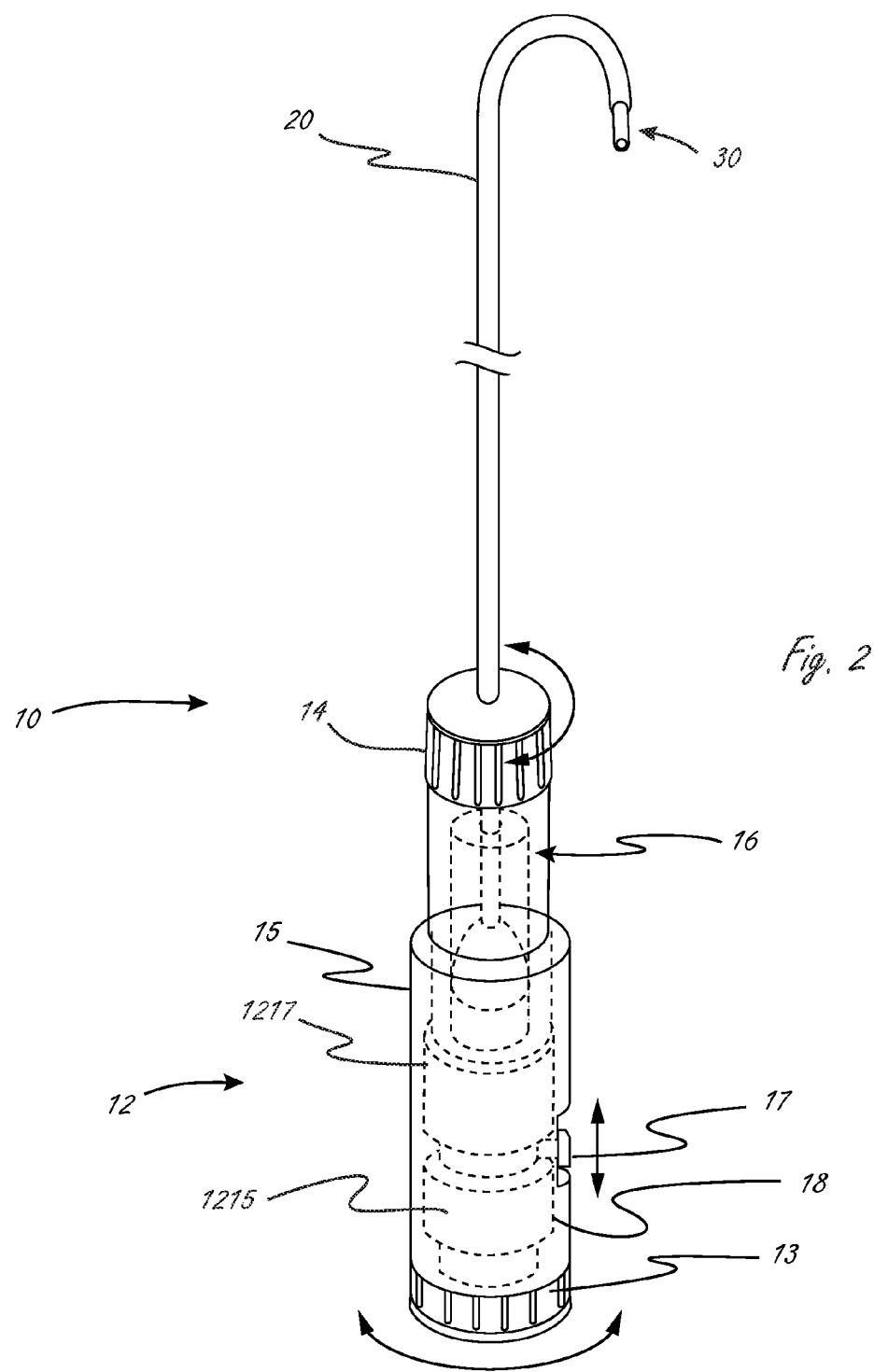

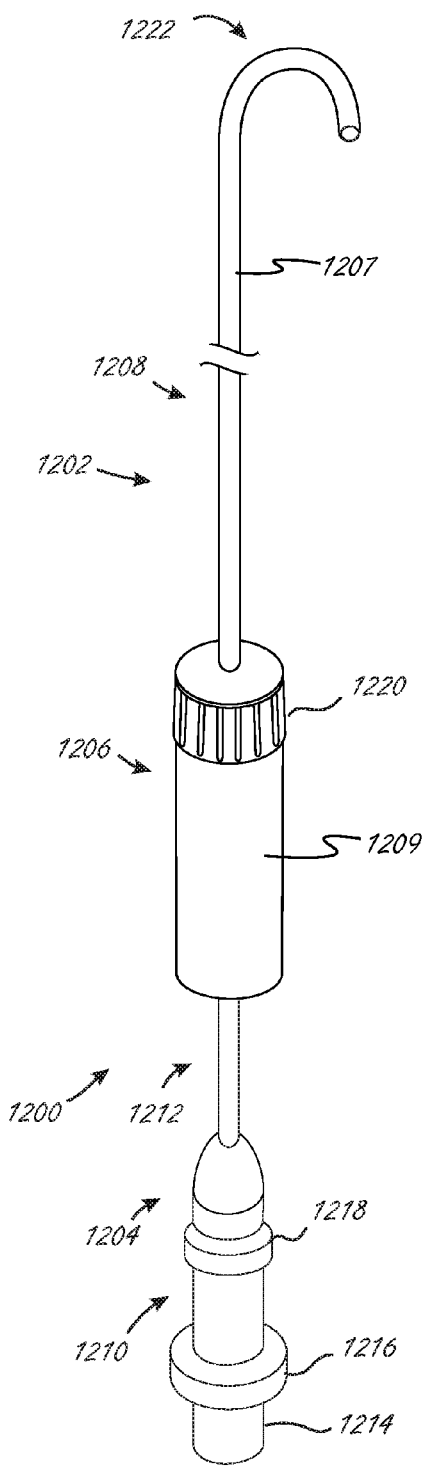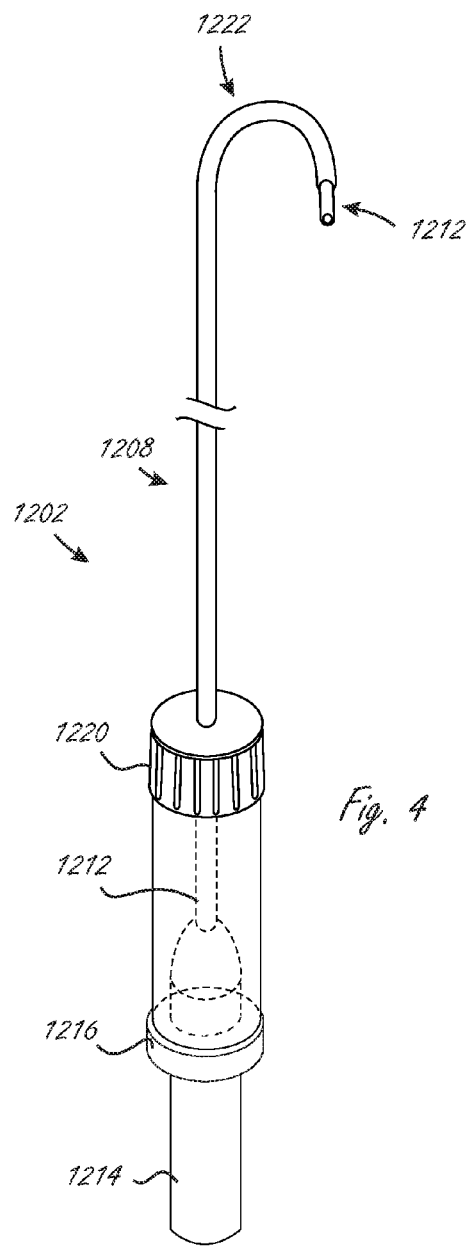
Fig. 3
Fig. 4

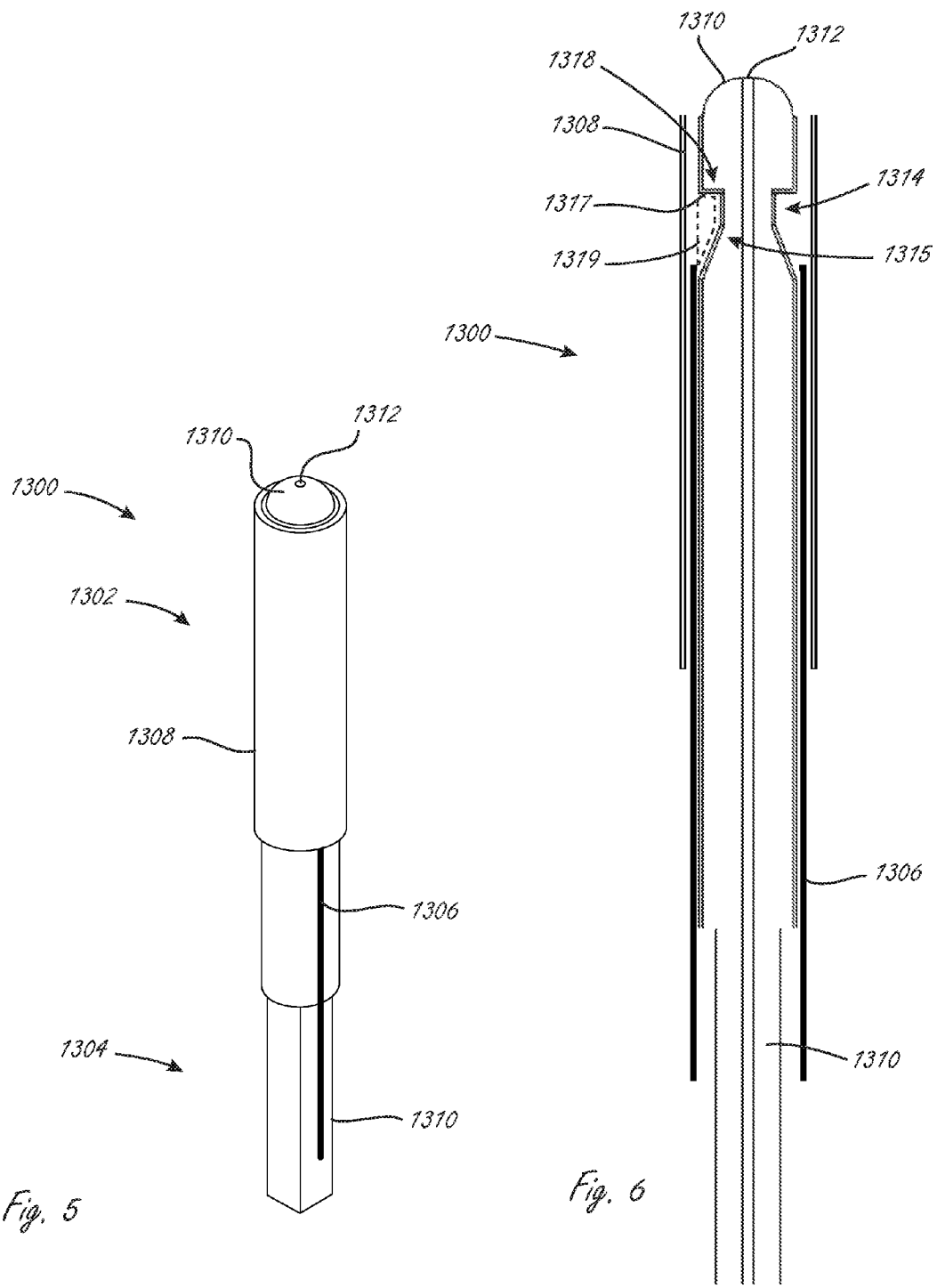

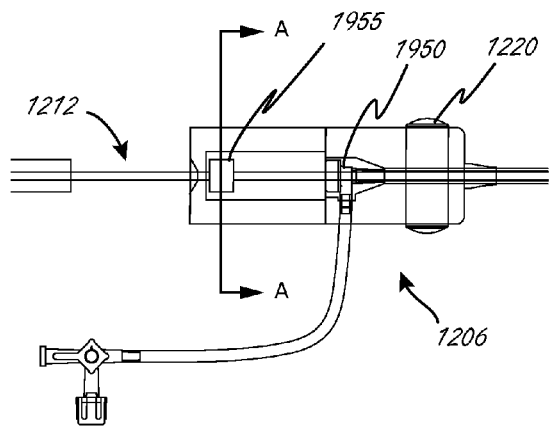
Fig. 9A
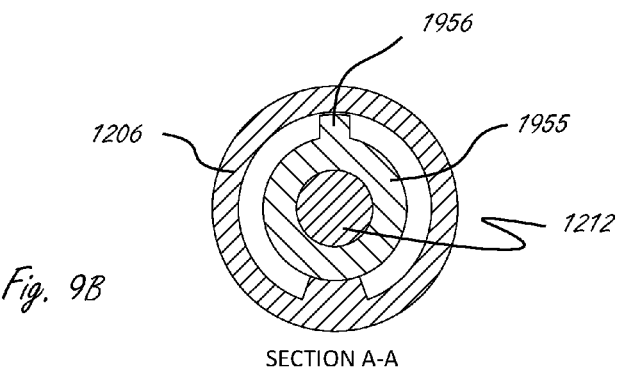
Fig. 9B
SECTION A-A
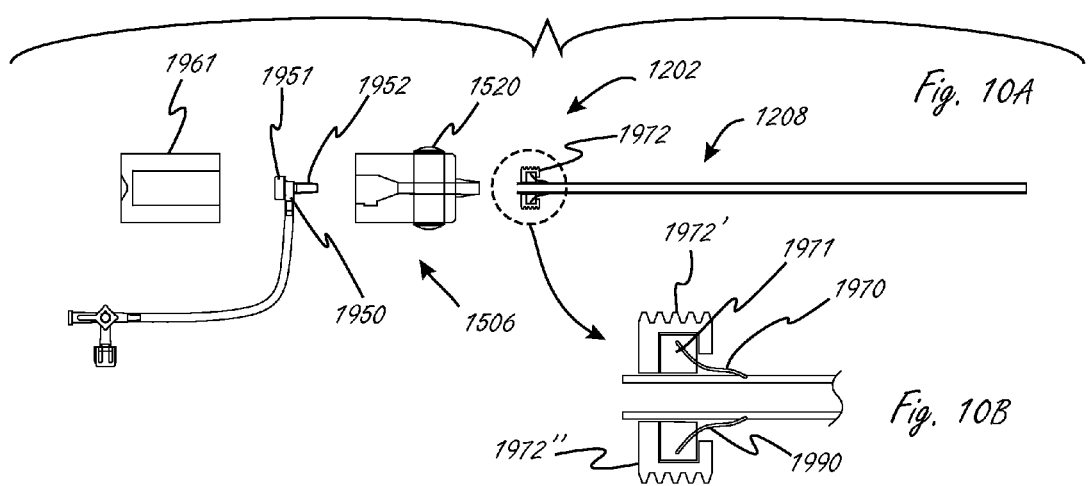
Fig. 10A
Fig. 10B

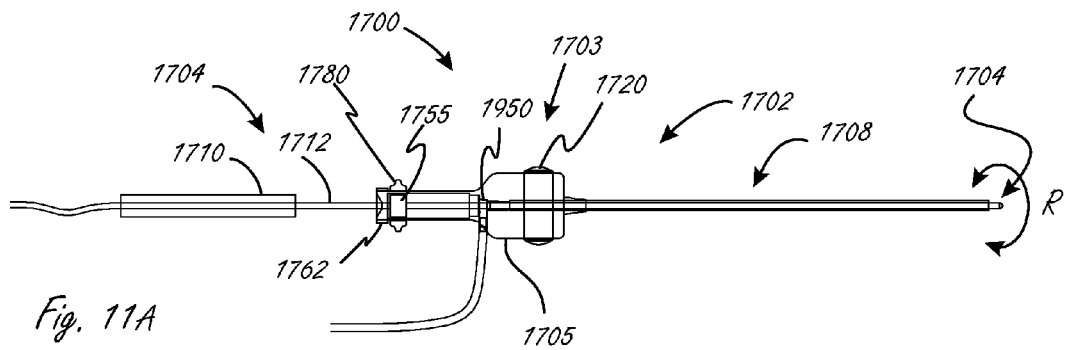
Fig. 11A
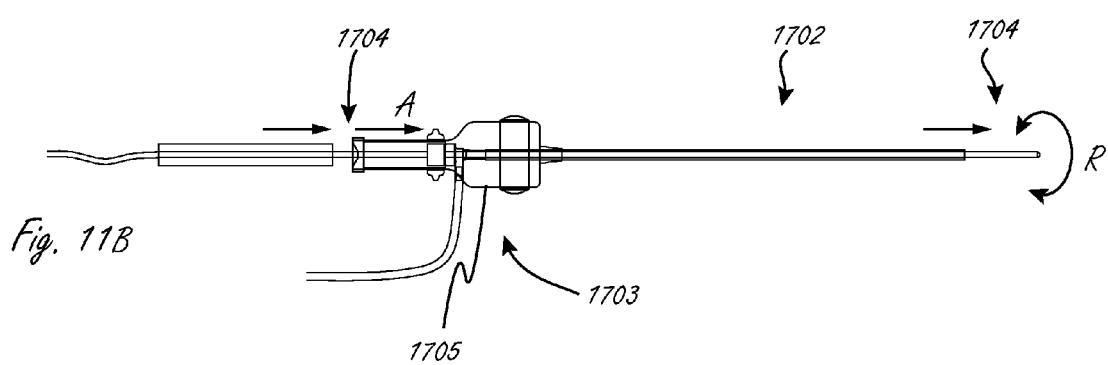
Fig. 11B
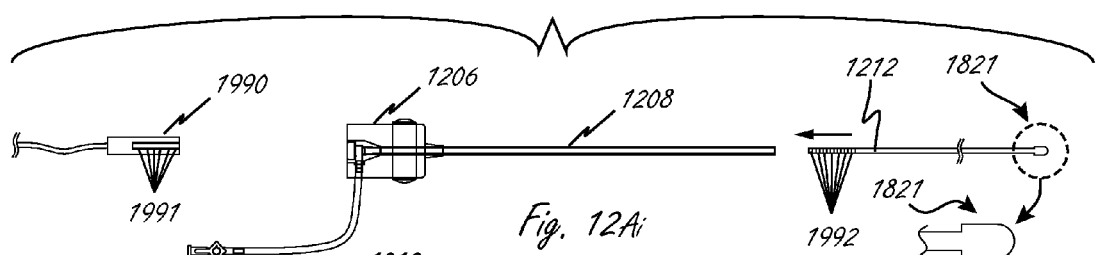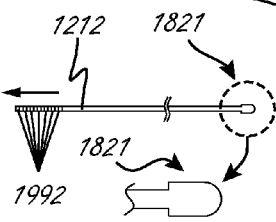
Fig. 12Ai  Fig. 12Aii
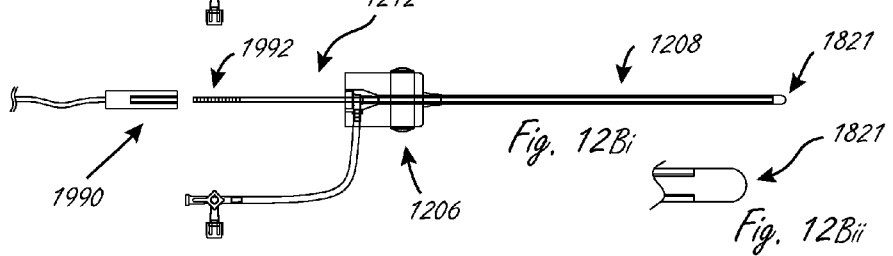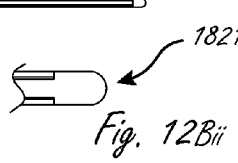
Fig. 12Bi  Fig. 12Bii
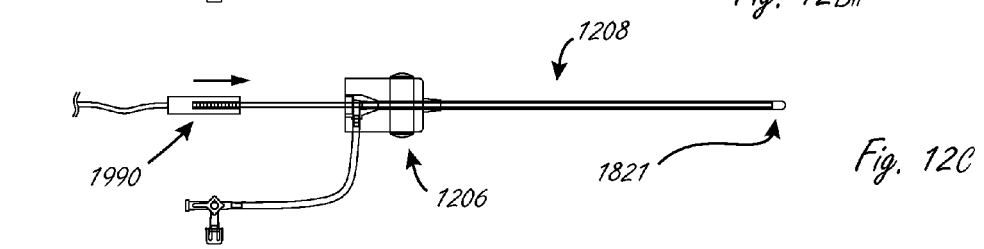
Fig. 12C

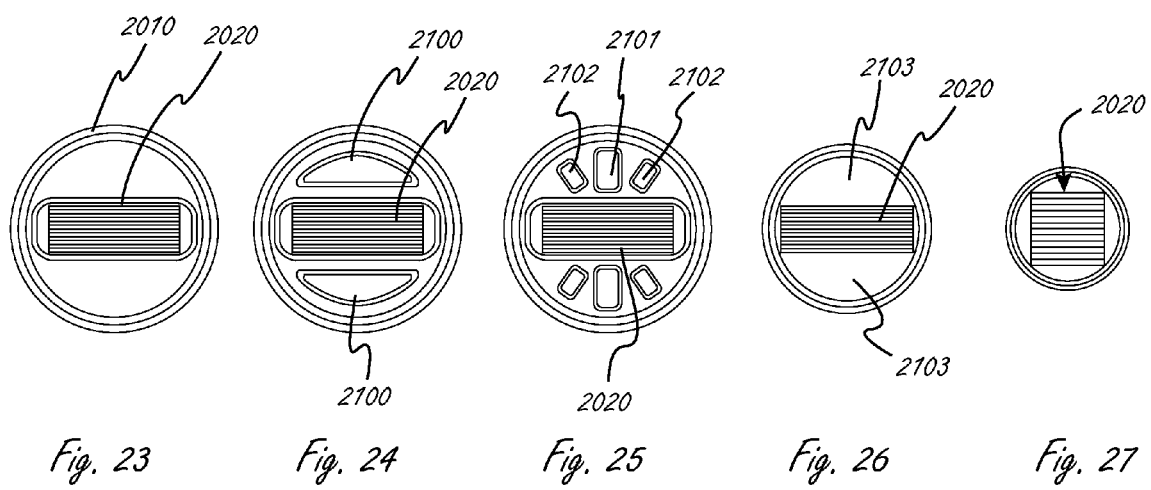

MEDICAL DEVICES AND METHODS OF USE

CROSS-REFERENCE TO RELATED APPLICATIONS

This application is a continuation of International Application No. PCT/US2017/042859, filed Jul. 19, 2017, which claims priority to the following U.S. Provisional Applications: U.S. Provisional Application No. 62/364,268, filed Jul. 19, 2016, and U.S. Provisional Application No. 62/404,711, filed Oct. 5, 2016, each of which are incorporated herein by reference.

INCORPORATION BY REFERENCE

All publications and patent applications mentioned in this specification are herein incorporated by reference to the same extent as if each individual publication or patent application was specifically and individually indicated to be incorporated by reference.

BACKGROUND

A wide variety of intravascular medical devices are known. After the medical device has been used in a subject, it may be desirable to reuse that medical device, or at least a portion of the medical device in another subject, rather than using an entirely new medical device, or an entirely new portion of the medical device. One reason for the desire to reuse at least a portion of the medical device can be the cost of at least a portion of the medical device. Rather than buying a new medical device or portion thereof, it may be less expensive to reuse the device or portion thereof again. If the device or a portion thereof has been exposed to a bodily fluid (e.g., in a blood environment), the medical device generally needs to be cleaned and re-sterilized (and perhaps disassembled to some extent) before being used again in another subject. Some non-sellers of the device attempt to clean the device and then resell it for subsequent uses. Downsides to this approach include the device being handled and cleaned by inexperienced individuals, who may damage the device, rendering it unsafe for subsequent uses. There is a need to have a more reliable, safe, and/or predictable practices in place to reuse medical devices that have been exposed to bodily fluids (e.g., in a blood environments).

Additionally, there are limitations on the use of some medical devices, such as, without limitation, ultrasound imaging devices. Improved systems, devices, and methods that facilitate better control and usability of medical device are also needed.

SUMMARY

One aspect of the disclosure is a method of disassembling a system exposed to a bodily fluid of a subject, the system including a medical tool (optionally an ultrasound probe), a steerable shaft, and a handle assembly. The method includes: providing a handle assembly, a steerable sheath that has been exposed to a bodily fluid environment of a subject, and a medical tool (optionally an ultrasound probe) that has been exposed to the bodily fluid environment of the subject, the handle assembly in operable communication with the steerable sheath and the medical tool, the handle assembly including a handle body with an outer surface that can be gripped by a user, a first actuator adapted to be moved relative to the handle body, and a second actuator adapted to be moved relative to the handle body, the steerable sheath having a distal deflectable region that is in operable communication with at least one pull wire, wherein the first actuator is in operable communication with the pull wire such that actuation of the first actuator relative to the handle body causes deflection of the distal deflectable region, and wherein the second actuator is adapted to be rotated relative to the handle body and is also adapted to be moved axially relative to the handle body, and wherein the second actuator is in operable communication with the medical tool such that axial movement of the second actuator relative to the handle body causes axial movement of the medical tool relative to the distal end of the steerable sheath, and such that rotation of the second actuator relative to the handle body causes rotation of the medical tool relative to the distal end of the steerable sheath, the medical tool having a distal portion that can include an ultrasound transducer, the distal portion extending further distally than a distal end of the steerable sheath and having an outer dimension greater than a dimension of a lumen of the steerable sheath in which the medical tool is disposed, the medical tool further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the second insulation layer defining a contact, the contact electrically coupled to an electrical contact on a printed circuit board.

The method can further include electrically disconnecting the contact from the electrical contact on the printed circuit board.

The method can further include moving the medical tool distally relative to the steerable sheath and out of the distal end of the steerable sheath.

The method can optionally further include cleaning at least a portion of the medical tool, the portion comprising a region of the medical tool that, prior to the moving step, does not extend outside of the steerable shaft and optionally comprises a region that, prior to the moving step, was disposed within the handle assembly. The method can optionally further include, at some time after the cleaning step, electrically coupling the contact to either the printed circuit board or a different printed circuit board.

In some embodiments of the method, the medical tool comprises a plurality of flexible circuit strips, each of the plurality of flexible circuit strips comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the insulation member defining a probe contact.

The method can further include, at some time before the moving step, releasing the medical tool from a releasably secured engagement with a handle assembly component. Releasing the medical tool from a releasably secured engagement with a handle assembly component can include releasing the probe from a releasably secured engagement with a handle assembly component that is in direct or indirect operable communication with the second actuator.

One aspect of the disclosure is a method of removing a used electrical contact from a flexible circuit. The method can further include creating or preparing a new electrical contact on the flexible circuit from which the used electrical contact was removed.

One aspect of the disclosure is reusing a flexible circuit after a first electrical contact has been used and is not being used anymore to create an electrical connection. The first electrical contact can optionally be removed after its use.

One aspect of the disclosure is a method of removing an electrical contact from an ultrasound probe to reuse the ultrasound probe, comprising: providing an ultrasound probe that has an ultrasound transducer in a distal region, wherein the ultrasound probe includes at least one exposed region of a plurality of conductive traces, the exposed region defining a probe contact; and disconnecting the probe contact from the ultrasound probe.

Disconnecting the probe contact from the ultrasound probe can comprise cutting the probe contact from the ultrasound probe. The method can further comprise exposing the plurality of conductive traces in a new region in which they were previously unexposed, the new region defining a new probe contact. Exposing the plurality of conductive traces in a new region can comprise any of the following: removing an adhesive layer from the ultrasound probe contact, ablating a portion of an insulation covering the conductive traces, using a laser to ablate away a region on insulation material, and dissolving at least a portion of insulation material with a solvent. The method can further comprise electrically coupling the new probe contact to an electrical contact on a printed circuit board.

One aspect of the disclosure is a flexible circuit that includes a first electrical contact, and also includes at least one additional electrical contact that can be created or prepared on the flexible circuit for use after the first electrical contact has been used and is not being used anymore to create an electrical connection.

One aspect of the disclosure is a flexible circuit strip, comprising: an elongate substrate; a plurality of elongate conductive traces disposed on and extending along the substrate; first and second covering elements disposed on and covering the plurality of conductive traces, wherein the first and second covering elements are axially separated from each other, and wherein the first and second covering elements define therebetween a new probe contact comprising the plurality of conductive traces; and a removable covering element disposed over the new probe contact, the removable covering element adapted to be removed from the plurality of conductive traces to expose the plurality of conductive traces at the location of the new probe contact.

The strip can further include at least a third covering element disposed on and covering the plurality of conductive traces, and axially spaced from the second covering element, the second and third covering elements defining therebetween a second new probe contact, and a second removable covering element disposed over the second new probe contact, the second removable covering element adapted to be removed from the plurality of conductive traces to expose the plurality of conductive traces at the location of the second new probe contact.

One aspect of the disclosure is an integrated medical tool, comprising: a handle assembly, a steerable sheath, and a medical tool (optionally an ultrasound probe), the handle assembly in operable communication with the steerable sheath and the medical tool, the handle assembly including a handle body with an outer surface that can be gripped by a user, a first actuator adapted to be moved relative to the handle body, and a second actuator adapted to be moved relative to the handle body; the steerable sheath with a distal deflectable region that is in operable communication with at least one pull wire; and an elongate medical tool with a distal portion that comprises a working end (optionally an ultrasound transducer), at least a portion of the elongate medical tool disposed within the steerable sheath, the elongate medical tool in operable communication with the second actuator, wherein the first actuator is in operable communication with the at least one pull wire such that actuation of the first actuator relative to the handle body causes deflection of the distal deflectable region, and wherein the second actuator is adapted to be rotated relative to the handle body and is also adapted to be moved axially relative to the handle body, and wherein the second actuator is in operable communication with the elongate medical tool such that axial movement of the second actuator relative to the handle body causes axial movement of the elongate medical tool relative to the distal end of the steerable sheath, and such that rotation of the second actuator relative to the handle body causes rotation of the elongate medical tool relative to the distal end of the steerable sheath.

The second actuator can interface with the handle assembly such that the interface with the handle assembly restricts at least one of the following: axial movement of the second actuator in both the proximal and distal directions within a fixed range of motion, and rotational movement of the second actuator in both directions of rotation within a fixed range of motion.

The first actuator can be adapted to be rotated relative to the handle body such that rotation of the first actuator relative to the handle body causes deflection of the distal deflectable region.

The medical tool can extend further proximally than a proximal end of the steerable sheath and optionally further proximally than the handle body.

In some aspects the disclosure herein relates to medical devices, systems, apparatuses, and their methods of use, methods of assembly, and disassembly. In some embodiments, the disclosure relates to steerable medical devices, or at least medical devices that are steered via a separate steerable shaft. Steerable devices, as that term and derivatives of that term are used herein, include any type of medical device that may benefit from being steered, bent, or deflected, directly or indirectly.

In some aspects the disclosure relates to steerable medical tools. When a steerable medical tool is described herein it is merely an example of the steerable medical devices described herein. Steerable delivery devices can be used to deliver, or guide, any type of suitable medical device or instrument therethrough to a target location within a patient's body. For example, a steerable delivery device can be used to deliver, or guide, a medical device into body lumens or cavities such as, for example without limitation, a blood vessel, an esophagus, a trachea and possibly adjoining bronchi, any portion of the gastrointestinal tract, an abdominal cavity, a thoracic cavity, various other ducts within the body, the lymphatics, one or more chambers of the heart, etc. Once a steerable medical device has gained access to a target location within the subject, the tool can be used to carry out one or more medical interventions. In some methods of use, the steerable device described herein is tracked along a previously positioned guide wire, the positioning of which is known in the art. In some embodiments the steerable concepts described herein can be applied to steerable medical tools such as catheters that have any diagnostic and/or therapeutic functionality.

In some embodiments herein, a medical device (which may also be referred to herein as a medical tool or tool) is integrated with a steerable sheath prior to delivery of the medical device to target tissue. For example, a medical device may be integrated with any of the steerable sheaths herein.

As used herein, a medical device or tool can be any type of medical device, including devices with diagnostic and/or therapeutic functionality. Integrated medical devices include catheters configured to provide functionality using at least a distal working region. A catheter with a distal tip electrode and associated components extending along its length is a mere example of a medical device that can be integrated with steering capabilities herein. A device with one or more ultrasound transducers, optionally for ultrasound imaging, can be any of the medical tools herein.

Another aspect of the disclosure relates to electrical connections between a connector and contacts that are in electrical communication with a working region, optional at a distal end, of a medical device.

BRIEF DESCRIPTION OF THE DRAWINGS

FIG. 1A illustrates an exemplary embodiment of a system that integrates steering and a medical device.

FIG. 1B illustrates a cross section A-A of the steering and device portion of the medical device of FIG. 1.

FIG. 2 illustrates an exemplary integrated system that includes a handle assembly with a plurality of actuators, a steerable sheath and medical tool.

FIGS. 3 and 4 illustrate an exemplary embodiment of a system in which the steerable portion can have a cross section equal to that shown in FIG. 2.

FIGS. 5 and 6 illustrate exemplary distal regions of a system in which the steerable portion can include a cross section as illustrated in FIG. 1B.

FIGS. 9A and 9B illustrate a portion of an exemplary system in which a tool lock and handle are configured to limit the range of medical device rotation.

FIGS. 10A and 10B illustrate an embodiment of a system that includes a steerable sheath that has exemplary modular features to aid in reposing the device.

FIGS. 11A and 11B illustrate an alternative embodiment of a system wherein a tool lock is contained within a sheath handle but coupled to an outer control.

FIGS. 12Ai, 12Aii, 12Bi, 12Bii, and 12C illustrate a concept where a medical tool contains a proximal electrical connector containing a plurality of electrical contacts.

FIGS. 23, 24, 25, 26, and 27 illustrate alternate exemplary embodiments of cross-sections of a bundled stack in a lumen, which can be incorporated into any the systems herein.

DETAILED DESCRIPTION

Figure 7:
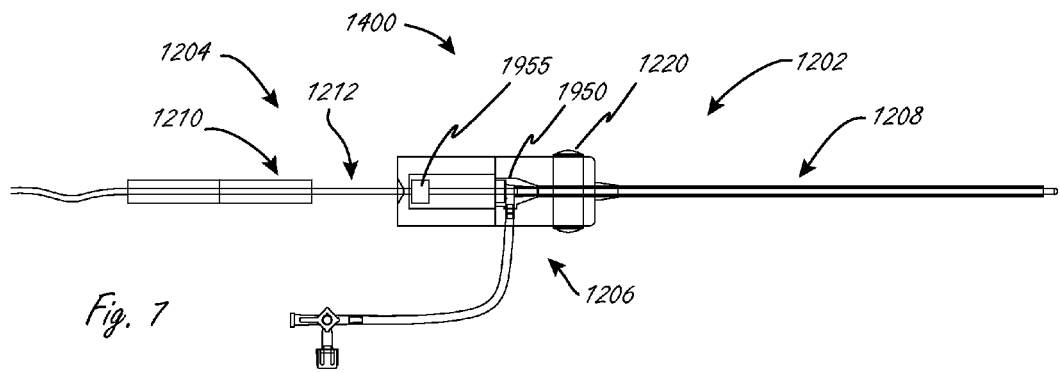
FIG. 7 illustrates a system comprising a medical tool inside a steerable sheath, designed to have modular components that are provided to the user in an integrated manner.

FIG. 1A illustrates an exemplary embodiment of a system that integrates steering and a medical device. System 1000 includes handle assembly 1002 and steering and medical device portion 1004. Steering and medical device portion 1004 includes a proximal portion 1006 and steerable portion 1008. The system is adapted so that handle assembly 1002 can be actuated to cause steering of the steerable portion 1008, and optionally can be further actuated to cause movement of medical device 1010 relative to steering and medical device portion 1004. In this exemplary embodiment, handle assembly 1002 includes first actuator 1001, second actuator 1003, and third actuator 1005. First actuator 1001 is adapted to be actuated (in this example rotated) relative to handle body 1007 to cause the steering of steerable portion 1008, and specifically steering outer sheath 1102. Steerable portion 1008 in this embodiment can be steered, or bent, into the configuration shown in FIG. 1A in solid lines, and can also be steered into the configuration shown in dashed lines, or anywhere in between, and in some embodiments the opposite steering function is limited to simply straightening the shaft from an initial bent configuration, such as the solid line bent configuration in FIG. 1A. The term "steer" in this disclosure means to deflect or bend, optionally via actuation of at least one pull wire, but in some instances the term can include shaft rotation (torquing) and axial movement. The term "pull wire" herein refers to any element that may transmit a tensile force from the proximal end of the device to the distal end region. Pull wires may be comprised of metal wire such as stainless steel or nickel titanium, either solid or stranded/braided, or it may be comprised of a polymer such as Kevlar, polyethylene, ptfe, eptfe, etc., preferably stranded/braided, but also in monofilament form. The wire cross-sectional diameter can be in the 0.005"-0.012" range, although braided or stranded wire may flatten or ovalize in the device lumen. Optional second actuator 1003 is adapted to be actuated relative to handle body 1007 (in this example rotated) to cause rotation of medical tool 1010 relative to shaft 1102 (labeled as rotation movement "R"), and optional actuator 1005 is adapted to be actuated relative to handle body 1007 (in this example axially) to cause axial (distal-proximal) movement of medical device 1010 relative the outer sheath 1102. Proximal portion 1006 is not configured to bend significantly when steerable portion 1008 is steered (bent/deflected), although the proximal portion may flex and bend to conform to the anatomy within which it is used. In many embodiments, this is accomplished by constructing the steerable portion 1008 from a softer or less rigid material and/or composite construction than the proximal portion 1006.

The embodiment shown in FIG. 1A is an example of an apparatus that includes an integrated handle assembly that is in operable communication with both a steerable outer shaft and an inner medical tool. The handle assembly is integrated in that it is assembled and constructed to be in operable communication with the outer shaft and the inner medical tool prior to packaging and use. "Integrated" as that term is used in the context of an integrated handle assembly refers to a handle assembly in which at least one part of the handle assembly has to be broken or taken apart before the medical tool can be removed from within the outer shaft.

FIG. 1B illustrates an exemplary cross section A-A (shown in FIG. 1A) of the steering and device portion 1004, and specifically in the steerable portion 1008. In this embodiment medical device 1010 is sized and configured to be disposed within a steerable sheath. The steerable sheath includes an outer shaft 1102 and a set of pull wires 1104, which are axially fixed in a distal region of steerable portion 1008.

The medical tool in FIGS. 1A and 1B can be, for example, any medical tool herein, such as an ultrasound tool. When "ultrasound probe" is used herein, it generally refers to an elongate tool that includes at least one ultrasound transducer and one or more conductive elements that electrically connect the at least one ultrasound transducer to a proximal region of the elongate tool. A proximal region of the ultrasound probe includes, or is modified to include, at least one proximal contact, which is in electrical communication with the at least one ultrasound transducer, and which can be put into electrical communication with, optionally via attachment to, an electrical contact on another device, cable, or connector.

FIG. 2 illustrates an exemplary system 10 that is adapted to function similarly to the system in FIGS. 1A and 1B, and also illustrates exemplary internal components of handle assembly 12 (internal components shown as dashed lines). Handle assembly 12 is integrated and in operable communication with outer steerable shaft 20 and medical tool 30. Handle assembly 12 includes actuator 14 that is adapted to, when actuated relative to handle body 15, cause steering of steerable shaft 20. Actuator 14 is in operable communication with steerable shaft 20 via steering control 16 disposed in handle assembly 12. Medical tool 30 includes a proximal portion 18 disposed within and incorporated into handle assembly 12. Actuator 13 is in operable communication with medical tool 30, and actuation of actuator 13 (in this example rotation) relative to handle body 15, causes rotation of medical tool 30 relative to outer shaft 20 via rotation control 1215. Optional third actuator 17 is also in operable communication with medical tool 30, and is adapted to be actuated, in this embodiment, axially (relative to handle body 15), to cause axial movement of medical tool 30 relative to outer steerable shaft 20 via axial control 1217.

The medical tool in FIG. 2 can be, for example, any medical tool herein, such as an ultrasound tool.

FIGS. 3 and 4 illustrate an exemplary embodiment of a system 1200 in which the steerable portion can have a cross section as shown in FIG. 1B. System 1200 includes steerable portion 1202 and medical tool 1204, both of which are configured to interface with each other. Steerable portion 1202 includes handle portion 1206 and a sheath portion 1208, which includes steerable portion 1222. Sheath portion 1208 includes an outer tubular member 1207. Medical tool 1204 includes handle portion 1210 and tool portion 1212, which includes at least one shaft and a working distal region at its distal end. Handle portion 1206 includes steering actuator 1220, which in this embodiment is adapted to be rotated relative to handle body 1209 to cause the steering of steerable portion 1222.

Medical tool 1204 is configured to be advanced through steerable portion 1202, both of which are configured to interface with each other. When advanced, tool portion 1212 of medical tool 1204 is advanced through sheath portion 1208 until its distal end is near the distal end of sheath portion 1208, and a portion of handle portion 1210 is advanced distally within handle portion 1206. Handle portion 1210 of medical tool 1204 includes handle 1214 and stabilizer 1218. Stabilizer 1218 is configured, along with an internal portion of handle portion 1206, to interface one another in a secure relationship to prevent relative movement therebetween in at least one direction. Handle portion 1210 also includes nut 1216, which is configured to interface with a proximal end of handle portion 1206. Stabilizer 1218 acts as an axial constraint for medical tool 1204, relative to steerable sheath 1202.

As shown in FIG. 4, a distal working region of tool portion 1212 is extending distally out of sheath portion 1208 when the medical tool 1204 and steerable sheath 1202 are stably interfacing with one another. In this embodiment the distal end of tool portion 1212 is not axially fixed relative to the distal end of sheath portion 1208.

The medical tool in FIGS. 3 and 4 can be, for example, any medical tool herein, such as an ultrasound tool.

Handle 1214 can optionally include at least one actuator that can cause the axial and/or rotational motion of the medical device relative to the steerable sheath. Thus, once the tool and sheath are stably interfaced, one or more tool handle actuators can control motion of the medical tool (e.g., rotational or axial). The tool and sheath can be interfaced after packaging and just prior to use, or they can be integrated before packaging. Handle 1214 can also include other controls that control the functionality of the medical tool.

FIGS. 5 and 6 illustrate an exemplary distal region of a steerable system that includes an inner medical tool. System 1300 includes steerable sheath 1302 and medical tool portion 1304. Steerable sheath 1302 includes outer member 1308 and one or more pull wires 1306, which are fixed distal to the steerable portion and configured such that, when a handle actuator is actuated, they are moved axially proximal to the steerable portion, which causes their relative axial movement in the steerable portion, which causes the steerable portion to be steered (as is described above). Pull wire 1306 can be parallel to the central axis in the steerable portion of the sheath.

In this merely exemplary embodiment, tool portion 1304 includes an elongate medical tool 1310 that includes an RF tip electrode at its distal end, and a guidewire lumen 1312, but the medical tool can be any other medical tool herein. In this embodiment tool 1310 and steerable sheath 1302 are configured so that the tool distal end (including the region very near the distal end) is axially immovable but rotationally movable relative to the steerable sheath 1302 distal end (including the region very near the distal end). To make the parts axially immovable and rotationally movable, outer member 1308 includes an extension 1314 that extends radially inward relative to the inner surface of outer member 1308 proximal to extension 1314. Tool 1310 includes a region with an outer configuration 1315 (radially inwardly shaped) that corresponds to the extension 1314. The two components similarly have shaped elements 1317 and 1318 distal to elements 1314 and 1315. The configuration of the tool and outer member therefore prevents distal and proximal movement of the tool relative to the outer member and therefore the steerable sheath when the tool and sheath are interfaced as shown. In this embodiment tool 1310 is rotationally free, or moveable, relative to steerable sheath. That is, while tool 1310 cannot move axially at the fixation location (which is distal to the steerable portion) it can be rotated. Being rotationally free can be beneficial if the medical tool, including one or more instruments thereon, should be oriented in or facing a particular direction.

Because the tool and the sheath are axially fixed distal to the steerable portion, the proximal end of the tool is configured to be able to move slightly axially during steering. For example, a spring built into the handle can allow the tool shaft to move slightly relative to the steerable sheath. Other ways of allowing for proximal axial movement can be incorporated as well.

The proximal end of system 1300 can include the two handle components such as those shown in the embodiment in FIGS. 3 and 4, and can be similarly interfacing, with the exception of the moderate axial movement of the tool at the proximal end.

In other embodiments the distal region shown in FIGS. 5 and 6 can be incorporated with a handle assembly shown in FIG. 1A or 2.

One aspect of the disclosure is a method of rendering two co-axial components that were previously axially movable axially immovable (axially fixing them). This aspect also includes methods of removing the axial fixation such that the components can again be axially moved. This can be considered releasable axial fixation. The axial fixation is created, in general, prior to advancing the system into a patient, and in some embodiments the axial fixation is created during manufacturing. The release of the axial fixation can occur during a refurbishing process, and the axial fixation can again be created during a refurbishing process.

In some embodiments the system can be modified to include a component whose volume can be modified (increased or decreased) to cause the axial fixation of the medical tool. In some embodiments the component has a configuration that changes to cause the axial fixation of the medical tool.

In some embodiments system 1300 is adapted so that extension 1314 is configured such that its volume can be modified to cause or release the axial fixation. In this particular modification, fillable annular volume 1319 (shown and labeled only once in the cross-section but it is understood that it exists on the other side due to its annular configuration) is adapted to be filled with a filling material, and such that the filling material can be removed as well. In these alternative embodiments the outer member includes an annular filling volume 1319 defined by the radially outer dotted line surface and by the radially inner portions of the previously described extension 1314. That is, extension 1314 is modified to include a fillable annular chamber or volume 1319, but outer surfaces of extension 1314 remain and define the annular fillable volume 1319.

When it is desired to allow tool 1310 and sheath 1302 to be relatively axially movable, such as during manufacture of the system, fillable volume 1319 remains at least partially un-filled, so that tool 1310 can be easily advanced or retracted axially within sheath 1302. When it is desirable to render tool 1310 and 1302 axially immovable, or fixed, (after they are in desired relative axial positions—such as during manufacturing or refurbishment), fillable volume 1319 is filled with a filling material so that the extension extends radially inward and becomes more rigid, preventing the axial movement of tool 1310 relative to sheath 1302. The extension in this embodiment is thus a reconfigurable axial restraint.

If it is desirable to axially move the tool 1310 and sheath 1302 at a later time (such as during refurbishment—e.g., at least one of cleaning and sterilizing), the fillable material can then be removed from volume (or chamber) 1319, making extension less rigid, so that tool 1310 can be axially moved relative to sheath 1302.

In these alternative embodiments extension 1314 can be considered expandable and unexpandable; fillable and unfillable; reconfigurable; configured and adapted to have a stiffness that can be modified; configured so that its rigidity can be modified; and having a volume that can be modified.

In some embodiments the fillable material can be inserted and removed from annular fill volume 1319 with a fill device such as a needle.

In one exemplary use, tool 1310 is axially advanced to the position in FIG. 6, and fill volume 1319 is thereafter filled with a filing material to axially fix tool 1310 and sheath 1302 (e.g., during manufacture or refurbishment). The method can also include removing the filling material and axially moving at least one of the tool 1301 and sheath 1302 (e.g., during refurbishment).

In an exemplary embodiment the filling material can be modified from a solid to liquid, and visa-versa, by changing its temperature. In some embodiments the fillable (also referred to herein as "filling") material is solid at operating temperature to increase the volume or rigidity of extension 1314, but can be melted (or made less viscous) to allow it to be removed from annular volume 1319.

In some embodiments the filling material is a wax. The wax can, in some embodiments, have a melting point less than a polymeric material of an adjacent component, such as an inner or an outer member.

This concept of creating axial fixation (and allowing removal of the axial fixation) by, for example, adding and removing a filling material, can be used to axially fix any two components herein, including an outer sheath of a steerable sheath and the medical tool within it.

FIG. 7 illustrates a system 1400 comprising a medical tool 1204 disposed partially inside a steerable sheath 1202. Medical tool 1204 and sheath 1202 can be any of the medical tools and sheaths described herein, even though they are labeled 1204 and 1202. While the steerable sheath 1202 is preferably "steerable", for example through the use of a pull wire or other functional deflection mechanisms (any of those set forth herein), it is understood that this "steerable" sheath (or any steerable sheath herein) could also be non-steerable in that it is just a straight tubular element, or has a fixed, non-deflectable distal curve shape. Steering may be also accomplished via torquing the sheath, with or without use of a deflection mechanism.

The system 1400 illustrated in FIG. 7 is designed to have modular components that are provided to the user in an integrated manner, but which can be disassembled after a procedure using a specialized process to clean, repair, and/or replace any of the modular components of the system. The system 1400 may then also be reassembled, sterilized and repackaged. This process, or in some cases a portion of this process, can be referred to herein as "reposing," or "refurbishment," and any system herein can be reposed or refurbished using any of the methods herein. The performance of system 1400 is optimized for the medical tool 1204 and sheath 1202 to work only with one another and not substitute other devices on the market that may have a similar function. Also, the reposing of the devices takes special care to ensure the continued safety and performance quality of the system.

In the disclosures that follow, many references are made to ways of separating various modular components of a system, either by breaking or using a controlled process. Depending on the embodiment, handle portion 1960 (see FIGS. 8A and 8B), rear handle 1961 (see FIG. 10), and handle lip 1962 (see FIG. 11A) can be separated from the handle assembly. Tool lock 1955, for example, can be separated from tool portion 1212 of medical tool 1204 or from handle assembly 1206. Tool connector 1210 (see FIG. 7) or 1990 (see FIG. 12A), for example, could be separated from tool portion 1212. Hemostasis valve 1950 assembly (see FIG. 7) could be separated from the handle assembly 1206. Sheath portion 1208 could be separated from handle assembly 1206. Outer member 2010 (see FIG. 16B) of tool portion 1212 could be separated from inner lead assembly 2011 and its internal electrical connections. Many similar controlled processes and materials could be used to enable the initial assembly and subsequent disassembly and reassembly of the components of any of the embodiments herein.

Any given process or combination of processes could be used at any one or all the aforementioned modular separation points. The processes include but are not limited to the following examples. Components could be bonded using a material that acts like an adhesive or mechanical lock, but which can be deformed with heat to remove the components. This includes materials such as wax and thermoplastic elastomers (polyurethane, polyethylene, polyamide, to name just a few). Materials such as hydrogels (such as those described previously herein) may be swollen with aqueous solutions to change their properties such that they soften or become lubricious enough to separate components. Sugar, salt, starch, or other similar materials in crystal or powder form could be used to create a mechanical interference fit between components, but then readily dissolved in an aqueous solution to separate the components. These materials could also be used as a matrix in a non-degradable material that then compresses like a foam once the crystalline structure is dissolved. Other polymers known to break down over time after contact with fluid (such as that introduced during use), including those also known in the art to be biodegradable, could be used in the system such that replacement due to their weakened properties would be mandated. Other materials could be used that lose their holding strength in the presence of a chemical solvent. Strong acids or bases could be used to dissolve certain metals and plastics. For example, silicone may swell and tear easily in the presence of heptane, hexane, or isopropyl alcohol. Where a liquid material is to be dispensed to alter the seal, the seal could be protected during use inside a protective space which can only be accessed with a special tool (such as a needle puncture diaphragm or luer activated valve).

Certain components may be joined using a solder or solder-like process, where reheating the solder will separate the components. In some embodiments the metallic joint could be separated using electrolysis. Mechanical interference could also be used to hold components together (e.g., screws, pins, thread, wedge, and the like). Ratcheting mechanisms (e.g., Zip-ties, belt-loop styles, roller-wedge, cam-actuated grips) could also be used to hold components together but require a manufacturer access to the parts to break and replace or use a tool to temporarily separate the components. Components could be held in place through magnetic attraction (magnet to magnet or magnet to iron). In particular embodiments, the magnetic hold could not be released without demagnetizing the magnets. This could be accomplished by physical breaking or mechanically fatiguing the magnet, raising the temperature of the magnet above its Curie Point (e.g., 80° C. for neodymium magnets), or applying an alternating current across the magnet to disrupt the dipoles. In another embodiment, parts could be engaged and held in place with a lock such as a bar fit into a hole or other capture feature (similar to a door lock). The bar could be heat set in a curve, or a hinge structure, that is normally engaged in the hole, but upon exposure to heat beyond a transition temperature, changes shape to back out of the hole (allowing parts to be disassembled). In a similar manner, the bar could be magnetized and when exposed to a magnetic field, forced out of the hole. Other similar mechanisms could use coils or other springs, or spring-actuated devices, which change shape in the presence of heat or a magnetic field to unlock. In another embodiment, components could be held together under hydraulic pressure (e.g., water or oil such as mineral oil or silicone oil), such as a sealed cylinder with a piston, a bellows, diaphragm, balloon, etc. To separate the components, the pressure may be vented by puncturing into or otherwise breaking the seal to the pressurized chamber. Opening or relaxing a valve to relieve the pressure could also be employed. In many cases, the process used to separate the parts will also contaminate or damage them enough to require replacement, further repair, and/or additional cleaning before reassembly and other subsequent processing steps.

Any combination of the exemplary processes above could also be used.

In any of the embodiments herein, a medical tool can be an ultrasound device, with one or more ultrasound transducers disposed at its distal region. For example, the ultrasound device may be an ultrasound imaging device, such as a 4D-ICE (intracardiac echocardiography) imaging tool.

FIG. 7 illustrates that tool portion 1212 of the medical tool 1204 may be rotatable within and relative to steerable sheath 1202 and may also be optionally capable of axial translation within the sheath. Tool lock 1955, which in FIG. 7 is disposed within the body of handle 1206, is secured to tool portion 1212 and may have one or more functions to constrain movement within sheath 1202 and/or control the functionality of medical tool 1204. FIG. 7 also illustrates a hemostasis valve assembly 1950 within the handle portion 1206 which is useful to keep blood or other fluids from leaking out from the proximal end of steerable sheath 1202, and to allow flushing of the luminal space between tool 1204 and the inner lumen of sheath 1202.

Figure 8A:
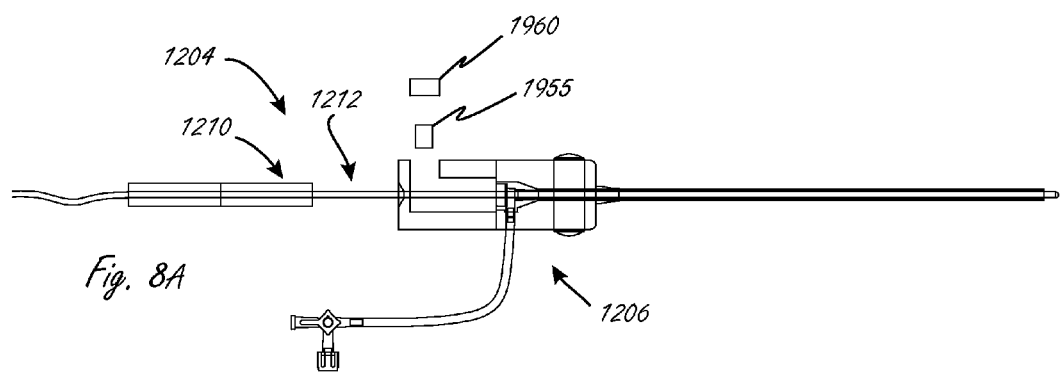
FIGS. 8A and 8B illustrate an embodiment where a sheath handle includes a removable or breakable handle portion.
Figure 8B:
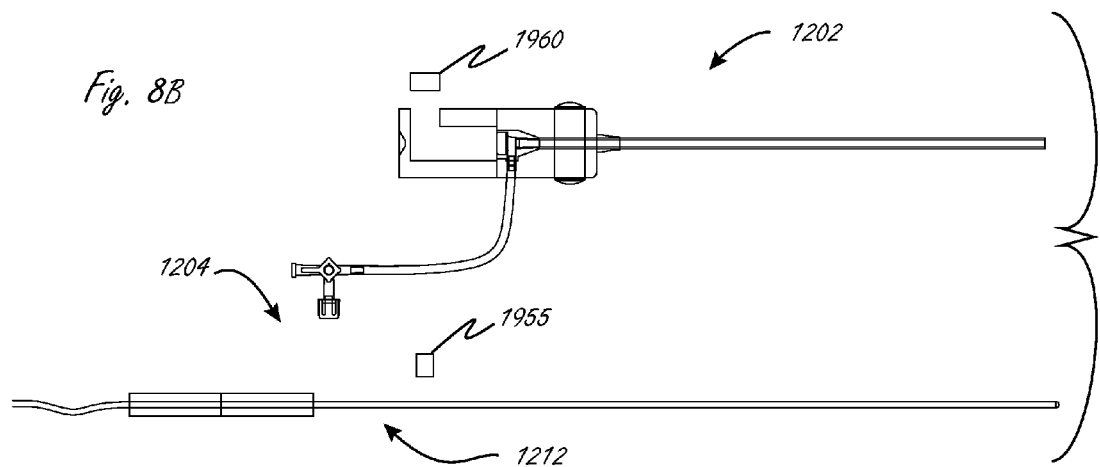

FIGS. 8A and 8B illustrate another embodiment of a system where handle assembly 1206 includes a removable or breakable handle portion 1960 that can be removed from handle assembly 1206 or broken from assembly 1206 to allow access to an interior space of handle assembly 1206. Once removed or broken, as shown in FIG. 8A, access is available to tool lock 1955 disposed with handle assembly 1206. Tool lock 1955 can then be disassociated from tool portion 1212. As shown in FIG. 8A. Once tool lock 1955 is removed, tool 1204 is can then be removed from sheath 1202, as shown in FIG. 8B.

In some embodiments, handle portion 1960 (and any other handle portion herein that can be removed or broken from a handle assembly) can be configured to interface with a corresponding component of handle assembly 1206 so that it can be stabilized relative to 1206 when in use, but can be removed from handle 1206 in a controlled manner without breaking an interface between handle 1206 and portion 1960. For example without limitation, the two parts could have a threaded interface. Alternatively, for example, portion 1960 can be configured so that the interface between it and handle assembly 1206 must be broken, but wherein the interface is such that breaking it can be done in a relatively easy and predictable manner.

One function of tool lock 1955 is to prevent removal of the medical tool 1204 from sheath 1202 to ensure system integrity as previously stated. A tool lock also limits the axial translation of the medical tool within the handle assembly by being physically constrained within the handle assembly. This may be desirable to ensure the medical tool is either not moved axially, or the movement is constrained to a safe and functional range for the medical tool beyond the tip of the sheath. In another embodiment, illustrated in FIGS. 9A and 9B, tool lock 1955 and handle assembly 1206 may both be configured to limit the range of medical tool rotation. This may be desirable to prevent a build-up of torque in one direction that could twist and damage portions of the outer member 2010 or an inner lead assembly 2011 (see FIG. 16).

As illustrated in FIGS. 9A and 9B, tool lock 1955 has a feature 1956, in this embodiment a radial protrusion on one side, that allows it to be rotated through an angle less than 360° in either direction. Handle assembly 1206 has a protrusion extending radially inward that is positioned and configured to engage with and stop movement of feature 1956, and thus tool lock 1955. Other torque limiters known in the art, including those that limit torque to a finite number of full rotations in a given direction, could also be employed. Axial travel and torque could also be limited by opposing magnets. Resistance would be encountered as a magnet in a tool lock approached (via axial or rotational travel), an opposing magnet positioned in the handle portion. Rotational limitation, an illustration of which is shown FIGS. 9A and 9B, can be incorporated into any of the systems herein.

In embodiments that include a tool lock, the tool lock rotational and/or axial movement may also have a friction fit with features within the handle such that it is moveable but does not rotate or slide back to the original position except by action of the user. For example, either or both the outer surface of the tool lock and an inner surface of the handle portion (such as handle portion 1960) may comprise a lubricious material such as PTFE, FEP, Delrin (Acetal). Unless formed from the same material, the mating material could be a smooth polished polymer or metal. The two parts could have a precise clearance or interference of, for example, up to 0.0002". The friction could also be controlled by a slight interference from just a portion of the surface of the tool lock with a portion of the handle portion (such as portion 1960). The interference could be a small integrated feature, and/or or a separate component which is mounted on an elastic material such as a compressible polymer (silicone, polyurethane, etc.), either solid or in foam form, or a metal or rigid polymer spring formed from a coil or flat ribbon. A slidable wedge could also be used to adjust the compression. The amount of compression interference could also be adjusted at the time of manufacture with a lead screw or a pressurized chamber driving the interference features together. During a reposing process this compression friction interference would need to be disassembled, and then reassembled and returned to manufacturer settings. In another embodiment, the compressive features could be assembled into the handle portion (such as portion 1960) to act directly on the tool portion 1212 without the need for the tool lock feature. While the tool lock is illustrated as integrated into tool portion 1212, it could also be integrated directly in to the tool handle portion 1210, which would be engaged into the sheath handle portion 1960. This is particularly applicable where axial translation of the medical tool 1204 relative to the sheath 1202 is not required.

Tool lock 1955 may also have an electronic or electromagnetic feature which senses the presence of handle portion 1960 (or other handle portion). Once a handle portion (e.g., portion 1960) is removed, the tool lock may disable the functionality of medical tool 1204. For example, the handle portion may include a magnet mounted in proximity to the tool lock. The magnet can hold a reed switch closed in the tool lock that completes a functional circuit in the medical tool. When the magnet is removed with the handle portion (e.g., portion 1960), the reed switch opens and disables the medical tool. Other proximity switches to accomplish the same function can also be used. The tool lock may also or alternatively disable the medical tool function once the tool lock is removed from the medical tool (e.g., as would be required to remove the medical tool from the sheath). For example, the tool lock could have a direct wired connection to the medical tool (for example, within the tool portion 1212) which disconnects from the medical tool upon tool removal. The medical tool could also include a proximity sensor in the tool portion 1212 which is disabled once the medical tool is removed from the sheath. For example, similar to that described above, a reed switch completing a functional circuit in the medical tool could be held closed by a magnet in the tool lock. Removal of the tool lock would then open the reed switch and disable the medical tool. Other proximity sensors known in the art could also be utilized. Replacement of the tool lock could re-enable the function; however, an additional reprogramming of the controlling tool software may also be made necessary to reset function of the medical tool once the software detects an interruption in the circuit. In a related scenario, the removal or breakage of handle portion (such as portion 1960) could interrupt a circuit in the tool lock which is sensed by the medical tool and/or more specifically, the controlling tool software. Function could then be restored to the tool by repairing, replacing, or reprogramming the tool lock, and the replacement and/or repair of the handle portion (such as portion 1960).

FIGS. 10A and 10B illustrates another embodiment of a system that has modular features to aid in reposing the device. In this embodiment, handle assembly 1506 may be disassembled through removal or breakage of handle rear component 1961 from the remainder of handle assembly 1506. This allows access to a tool lock (not shown but it could any tool lock described herein) as well as hemostasis valve assembly 1950. Depending on the configuration of the tool handle, the handle rear 1961 may be removed from the tool in the proximal direction (without removal of the tool lock), or the tool lock may be accessed more easily to remove the tool lock than the prior embodiment where only the handle portion 1955 was removed. In the present configuration hemostasis valve assembly 1950 may be accessed to remove and replace the valve assembly. Alternatively the valve assembly, including any of its individual components, could be removed, disassembled, cleaned, repaired, and replaced. Repair may only involve replacement of hemostasis seal 1951 in the assembly 1950. The seal could be of a slitted silicone or other soft polymeric compound known in the art, or any of the seals in this disclosure. The hemostasis valve assembly preferably includes a luer fitting 1952 on its distal end such that it could simply be pressed into and out of a mating luer fitting in the handle. Alternative fittings can also be used.

The steerable sheath 1202 may also be adapted to allow the sheath portion 1208 to be separated from the handle assembly 1506. Similar to other modular components, this could allow removal for cleaning, repair, or replacement. Sheath 1202 may be fitted with tensile elements to deflect the catheter tip. Tensile elements similar to these are illustrated in FIG. 10B as elements 1970. The one or more tensile elements 1970 are preferably secured permanently to a fastener 1971, such as by a welding, soldering, crimping, swaging, or adhesive/epoxy bonding process. If potting the ends in an adhesive/epoxy, the end of the tensile element is preferably formed into an enlarged ball, coil, loop, or other similar feature larger than the cross-section of the tensile element itself. Alternatively, the tensile element may be releasably secured with a set screw or other mechanical fastener. An enlarged welded ball end or a separate tube crimped to the proximal end of the tensile element may aid in mechanical capture of the tensile element 1970 in the fastener 1971. The fastener 1971 is configured to be acted on by an engagement feature 1972 and linked to the steerable actuator 1520. The engagement feature 1972 comprises a portion 1972' and 1972" each comprising a thread, one the reverse of the other. The actuator 1520 comprises a dual thread, one the reverse of the other, such that when actuator 1520 is rotated, portions 1972' and 1972" of the engagement feature are driven in opposite directions thereby causing the steerable section to deflect in one or another direction. The fastener may be designed to be readily disconnected and reconnected to the actuator for rapid and cost-effective processing during reposing. Alternatively, the tensile elements may be removably connected directly to the engagement feature without use of the fastener.

FIGS. 11A and 11B illustrate an alternative embodiment of an integrated medical device (e.g., ultrasound) or system 1700 that includes an integrated handle assembly, a steerable sheath, and a medical tool, and can be repurposed using any of the methods herein. In system 1700, the handle assembly 1703 is in operable communication with steerable sheath 1702 and medical tool 1704, the handle assembly 1703 including a handle body 1705 with an outer surface positioned to be gripped by a user, a first actuator 1720 adapted to be moved relative to handle body 1705, and a second actuator 1780 adapted to be moved relative to handle body 1705. Steerable sheath 1702 has a distal deflectable region (not labeled) that is in operable communication with at least one pull wire. In some embodiments, medical tool 1704 is an elongate ultrasound device with a distal portion that comprises an ultrasound transducer, at least a portion of the elongate ultrasound device is disposed within steerable sheath 1702, the elongate ultrasound device is in operable communication with second actuator 1780. First actuator 1720 is in operable communication with at least one pull wire such that actuation of first actuator 1720 relative to handle body 1705 causes deflection of the distal deflectable region of steerable sheath 1702.

Second actuator 1780 is adapted to be rotated relative to handle body 1705 and is also adapted to be moved axially relative to handle body 1705. Second actuator 1780 is in operable communication with the elongate medical device 1704 such that axial movement of the second actuator relative to handle body 1705 causes axial movement of elongate medical device 1704 (distal and proximal) relative to the distal end of the steerable sheath, and such that rotation of second actuator 1780 relative to the handle body 1705 causes rotation of elongate medical device 1704 relative to the distal end of the steerable sheath, as is shown as rotational movement "R" in FIGS. 11A and 11B.

Axial movement of the tool relative to the sheath, if the tool is an ultrasound imaging tool, is generally desirable in that it improves the probe's ability to image larger regions of the body after the probe has been steered to a particular location and allows the operator to more easily refine the field of view once the probe has been steered to a generally viable location.

System 1700 also includes optional tool lock 1755. Tool lock 1755 is contained within handle assembly 1703 but coupled to second actuator 1780. Tool lock 1755 and second actuator 1780 may be fitted with magnets, for example, to engage one another. Alternatively, one of the components could contain iron and the other a magnet. Tool lock 1755 is firmly and releasably coupled to tool portion 1712 of medical tool 1704. Advancing distally or retracting proximally second actuator 1780 moves tool lock 1755 distally or proximally, respectively. The resulting axially movement of actuator tool 1755 causes axially movement of medical tool 1704. Similarly, rotation of second actuator 1780 relative to handle body 1705 causes rotation of tool lock 1755, which causes the rotation of medical tool 1704 (shown as rotation "R" in FIGS. 11A and 11B). In this embodiment, the tool's axial movement (relative to the sheath) as well as its rotational movement (relative to the sheath) are limited within a fixed range of motion. In one embodiment, in order to remove medical tool 1704 from the steerable sheath 1702 (such as during refurbishment), handle rear lip 1762 could be removed or broken to remove tool lock 1755 (and remainder of the tool portion 1712) from handle 1706. In addition, second actuator 1780 could be decoupled from tool lock 1755. This may require custom fixtures to pry the coupled units apart, or the use of a special tool to demagnetize or otherwise alter the polarity (temporarily at least) of either the outer coupler or tool lock. As described previously, the tool lock may contain a feature to disable the tool function when the magnet or other proximity controller is removed. Rear lip 1762 is an illustrative and optional component, and the handle assembly can have different parts.

FIGS. 12A-12C illustrate an embodiment of a system in which the medical tool 1204 (which can also be any other medical tool herein) includes a plurality of electrical contacts 1992. FIGS. 12Ai and 12Aii illustrate the disassembled components. FIGS. 12Bi and 12Bii illustrate tool portion 1212 back loaded into the sheath portion 1208. FIG. 12C illustrates proximal tool connector 1990 (which can be attached, directly or indirectly with an energy console) connected to tool portion 1212 so the tool portion 1212 is in electrical communication with connector 1990. Tool portion 1212 is fitted on the proximal end with a plurality of mating electrical contacts 1992. Tool 1204 contains a distal working end 1821 (e.g., ultrasound imaging tool) which is larger in diameter than the lumen of the tool portion 1212, an illustration of which is shown in FIG. 12Bii. In this embodiment the outer dimension of tool portion 1212 and electrical contacts 1992 are sized to pass through a lumen of the sheath portion 1208, but the distal working end 1821 is too large to pass through the lumen. As a result, assembly of the tool through the sheath portion 1208 requires the proximal end of the tool portion 1212 be advanced through the distal tip of the sheath and advanced proximally until the electrodes exit the proximal end of the sheath handle 1206. This construction helps minimize the outer dimension of the sheath portion 1208 such that it is not necessarily larger than the distal working end 1821. In certain uses the distal working end may need to be at a maximum allowed dimension to accommodate electronic components and their connections, or, in certain applications, minimize the density of electrical current or acoustic energy to minimize overheating or cavitation of the tissue. The proximal electrical contacts 1992 may be discrete electrically conductive surfaces (e.g., discs, bars, strips, spheres, etc.), or circumferential or partially circumferential rings. In a preferred embodiment, the contacts are formed from the exposed conductive material of an otherwise insulated flex circuit (e.g. insulation is not disposed over the exposed conductive material). The mating contacts 1991 in the connector may be similarly designed to make contact. The contact surface may be annular or flat and preferably is spring loaded or otherwise mechanically compressed to make secure contact. The handle assembly in FIGS. 12A-C can be any of the handle assemblies herein; the steerable sheath can be any of the steerable sheaths herein; and the medical tool can be any of the medical tools herein. The front loading assembly can be used during the assembly of any system herein.

Figure 13A:
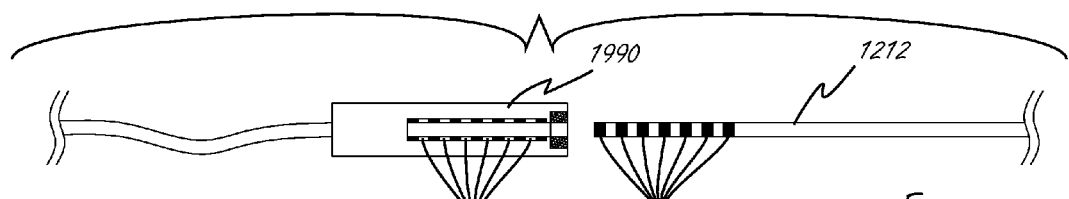
FIGS. 13A, 13B and 13C illustrate an exemplary proximal coupling between a medical tool and a connector.
Figure 13B:
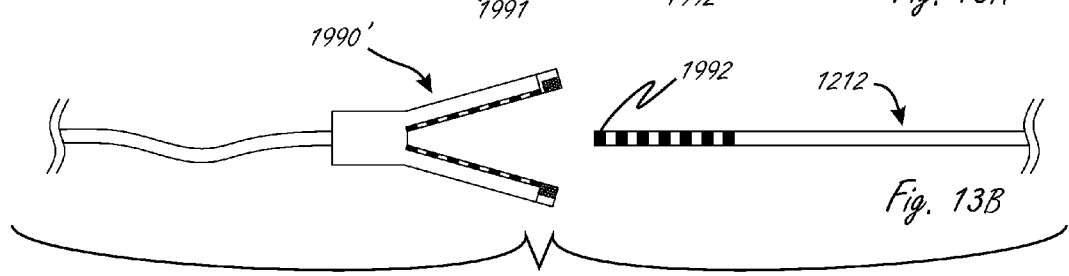
Figure 13C:
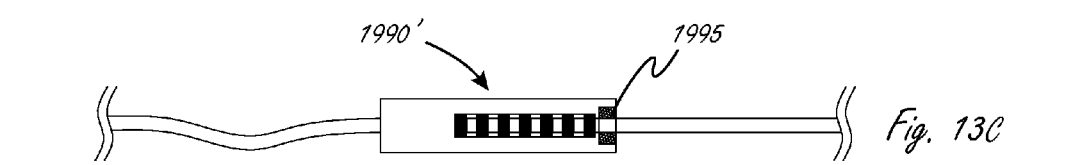

FIGS. 13A-13C illustrate an exemplary proximal portion of a system, and which can be the proximal portion of any of the systems herein. As illustrated in FIG. 13A, proximal contacts 1992 of the medical tool may be press fit into connector 1990 against the contacts 1991. Alternatively, as illustrated in FIG. 13B, connector 1990' can be adapted to open up to receive contacts 1991 before it is clamped down over contacts 1991, as shown in the closed configuration of FIG. 13C. The connector 1990' can be sealed with seal 1995 during manufacture. Seal 1995 may comprise, but is not limited to, a hydrogel, a wax, a silicone ring or gasket, or other means and combinations described previously in this disclosure. To repose the device, the connector 1990' contact must be broken or carefully disassembled to remove the shaft of tool 1212 in the distal direction through the sheath (such as a steerable sheath). Disassembly of seal 1995 may be accomplished by heating and melting the wax or other meltable substance, dissolving a dried material in an aqueous solution, and/or swelling a silicone with heptane or similar chemical compound.

Figure 14A:
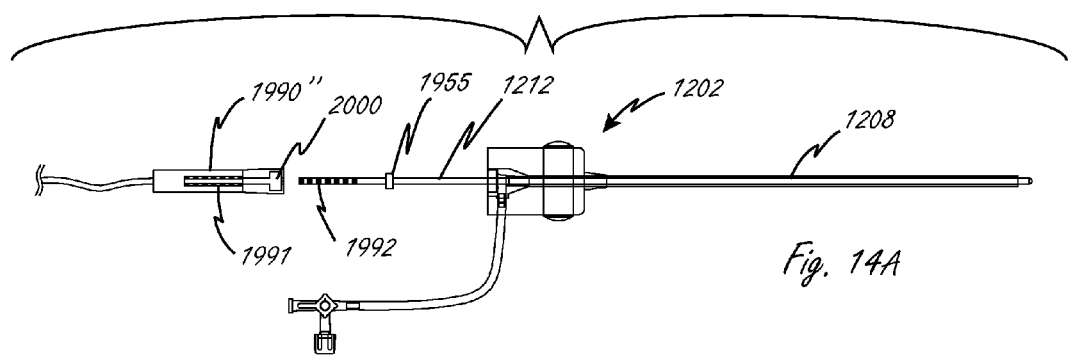
FIGS. 14A and 14B illustrate an exemplary system with a connector that contains an inner feature designed to enclose a tool lock attached to a tool portion.
Figure 14B:
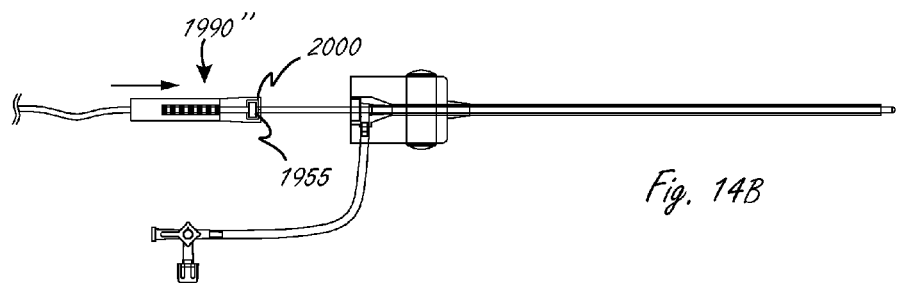

FIGS. 14A-14B illustrate a exemplary system similar to that of FIGS. 13A-13C with the exception that the connector 1990" contains an inner feature 2000 designed to stably interface with and enclose tool lock 1955 attached to tool portion 1212. FIG. 14A illustrates the system just before connection of the connector 1990" to the tool portion 1212, and FIG. 14B shows a completed connection. While tool lock 1955 is illustrated just distal to the proximal tool contacts 1992, it could also be configured on the proximal side of the contacts, with a corresponding inner feature 2000 location proximal to the connector contacts 1991. As described previously, the tool lock may contain a feature to disable the tool function when the magnet or other proximity controller is removed. In this embodiment, the disabling feature may alternatively be built into the connector 1990", particularly within the inner feature 2000, where the circuit connection in the cable leading back to a control console is dependent on the state of the disabling feature. Assembly and disassembly of the portion of the connector containing feature 2000 could be accomplished by the means described previously for the connector 1990 in FIG. 13, the handle portion of FIG. 8, or the rear handle of FIG. 10. The handle assembly in FIGS. 14A-B can be any of the handle assemblies herein; the steerable sheath can be any of the steerable sheaths herein; and the medical tool can be any of the medical tools herein.

In a variation of the embodiment in FIGS. 14A and 14B, the assembly of tool 1212 may require the "back loading" of tool 1212 through the distal end of the steerable sheath portion 1208, as described in the embodiment of FIGS. 12A-12C wherein the outer dimension of the tool and the electrical contacts are sized to pass through the lumen of the sheath portion, but the distal working end may not pass. In this embodiment of FIGS. 14A and 14B, the tool lock must be assembled after back loading the tool. During reposing, the tool lock would need to be removed to remove the tool 1212 from the sheath portion 1208, and repaired and/or replaced after cleaning and re-back loading the tool 1212 through the sheath portion 1208. In an alternate version of the embodiment, the tool 1212 may be assembled by "front loading" an insertion of the distal tip through the proximal handle end of sheath 1202. In this alternate embodiment of FIGS. 14A and 14B, tool lock 1955 does not necessarily need to be removable from the tool 1212.

As illustrated in FIGS. 14A-B, the clamping action of inner feature 2000 over tool lock 1950 results in a mechanical engagement of the two features such that axial translation and torque may be transferred from the connector 1990" to the tool 1212. This may provide the user with a more convenient means of gripping the tool 1212 to manipulate its position relative to the sheath 1202.

Figure 15:
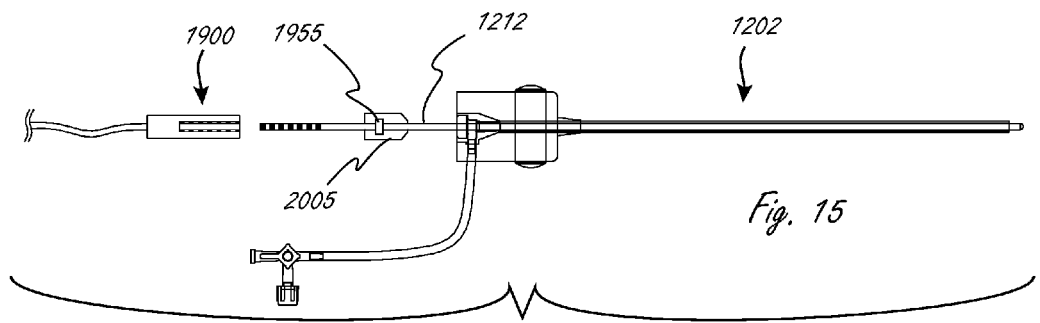
FIG. 15 illustrates an exemplary system that includes a separate torque device that could be attached to a medical tool to provide an ability to translate and torque the tool relative to a steerable sheath.

As illustrated in the exemplary system of FIG. 15, a separate torque device 2005 can be attached to the tool 1212 to provide a similar ability as above to translate and torque the tool 1212 relative to sheath 1202, but without the need to make a connection to connector 1990, as previously described in FIGS. 14A and 14B. The torque device 2005 may also be engaged over tool lock 1950 to provide enhanced mechanical engagement. Torque device 2005 could also serve a purpose similar to the inner feature 2000 in that tool function is dependent on the presence of the torque device 2005. As previously described in the embodiment of FIGS. 12A-12C, the torque device could be assembled onto the tool 1212 such that removal of the tool 1212 from the sheath 1202 is not possible without breaking the torque device and/or tool 1212, or without the use of a custom reposing process to remove the torque device. The handle assembly in FIG. 15 can be any of the handle assemblies herein; the steerable sheath can be any of the steerable sheaths herein; and the medical tool can be any of the medical tools herein.

Figure 16A:
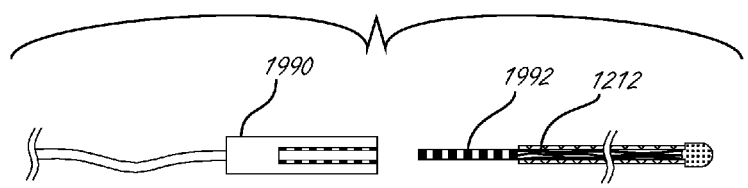
FIGS. 16A, 16B and 16C illustrate an exemplary tool that comprises an outer member and an inner lead assembly.
Figure 16B:
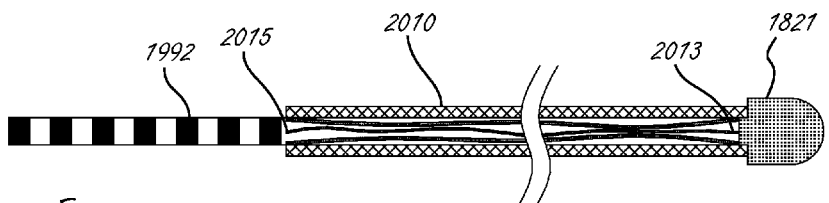
Figure 16C:
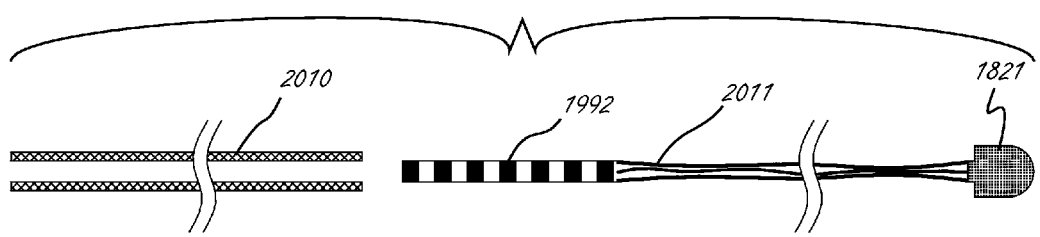

The embodiment of FIGS. 16A-C illustrates an exemplary medical tool where tool portion 1212 comprises an outer member 2010 and an inner lead assembly 2011. The inner lead assembly further includes a distal working end 1821 and proximal electrical contacts 1992. The outer member 2010 may be assembled and disassembled from the inner lead assembly as part of the reposing process. The outer member 2010 can be a tubular structure capable of transmitting torque via, for example, a braided composite construction. Outer member 2010 is reversibly sealed and secured to the inner lead assembly at locations 2015 and 2013 using processes previously described in this disclosure. FIG. 16B shows a larger view of the encircled region in FIG. 16A. FIG. 16C shows inner lead assembly 2011, distal working end, and proximal end removed from outer member 2010. The handle assembly in FIGS. 16A-C can be any of the handle assemblies herein; the steerable sheath can be any of the steerable sheaths herein; and the medical tool can be any of the medical tools herein.

The disclosure below relates generally to electrical connections and contacts in a medical device, optionally an ultrasound probe if not otherwise specified. The disclosure that follows can apply to any of the systems, or aspect of the systems, herein. The electrical connections, contacts, device, and methods can be integrated into any of the systems above, such as, without limitation, the handle assembly in FIG. 11.

One aspect of the disclosure includes methods of disassociating at least a portion of the system from other components, optionally as part of a reposing process. In some embodiments the medical tool includes one or more electrical contacts that are coupled to other electrical contacts, which are in electrical communication with an energy console, and examples of consoles are known in the ultrasound art.

Figure 17:
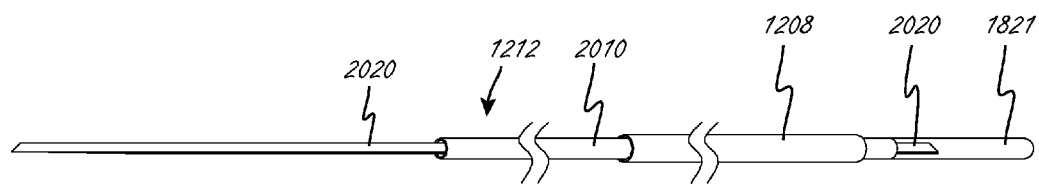
FIG. 17 illustrates an exemplary portion of an exemplary system that includes a bundle.

FIG. 17 illustrates merely a portion of an exemplary medical tool, such as an ultrasound probe, that can be electrically coupled directly or indirectly to an energy console, such as an ultrasound console.

The embodiment shown in FIG. 17 can be used in a manner similar in concept to the embodiment illustrated in FIGS. 12A-C, in that reposing the device involves disconnection of one or more proximal electrical contacts and moving the tool portion distally out of the distal end of the sheath portion. In this embodiment tool portion 1212 comprises at least a tool outer sheath or member 2010, distal working end 1821 (which can include at least one ultrasound transducer), and conductor bundle 2020. The conductor bundle 2020 extends from the distal working end 1821, through the tool outer member 2010 to a proximal connector (the connector and handle mechanism are not shown in FIG. 17 for clarity). In some embodiments the medical tool is used for ultrasound imaging, optionally where the distal working end 1821 comprises a two-dimensional (2D) array of piezo electric components mounted on an ASIC (application specific integrated circuit).

Figure 18:
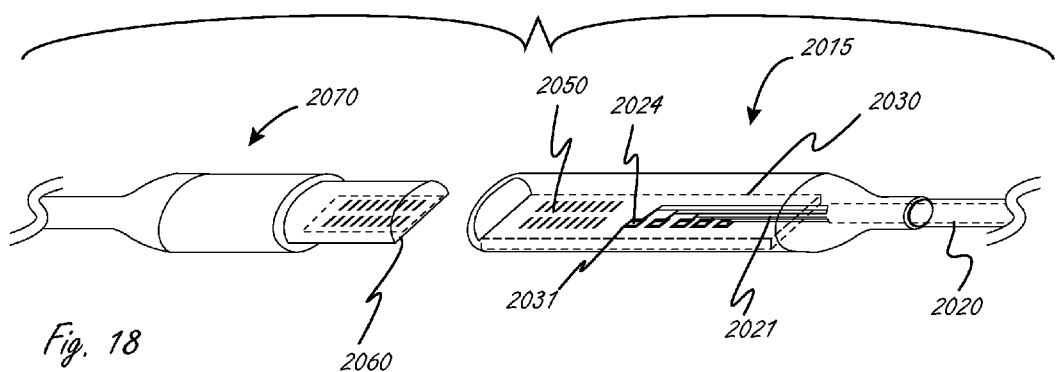
FIG. 18 illustrates an exemplary proximal end of a medical tool, the tool including a conductor bundle that extends into a proximal connector within which is housed a printed circuit board (PCB).

FIG. 18 illustrates a merely exemplary proximal end of a medical device (the medical device is shown on the right), and in this embodiment the medical device is an ultrasound probe. The proximal end 2015 of the medical device is adapted to be electrically coupled to connector cable 270, which is directly or adapted to be indirectly electrically coupled to an energy console, such as an ultrasound energy console. As illustrated in FIG. 18, conductor bundle 2020 extends from a distal region of the medical tool (distal region not shown) into a proximal connector 2015 within which is housed a rigid or flexible printed circuit board ("PCB") 2030. The connector bundle 2020 includes a plurality of contacts 2024 (examples of which are described below) that are attached to PCB board contacts 2031. Each individual trace from each contact 2031 is linked to individual exposed contacts 2050 on another portion, optionally more proximal, of the PCB. The individual PCB traces may also pass through other useful circuitry on the PCB. The exposed contacts 2050 are configured for a mechanical mating for electrical conduction to similar contacts 2060 on mating connector cable 2070, similar in concept to the proximal tool connector 1990 described previously, which links the tool 1204 to a user-interface console. Proximal connector 2015 can be incorporated into any of the systems, handles, steerable sheaths, medical tools, etc., herein, such as that shown in FIGS. 11A and 11B.

Figure 19A:
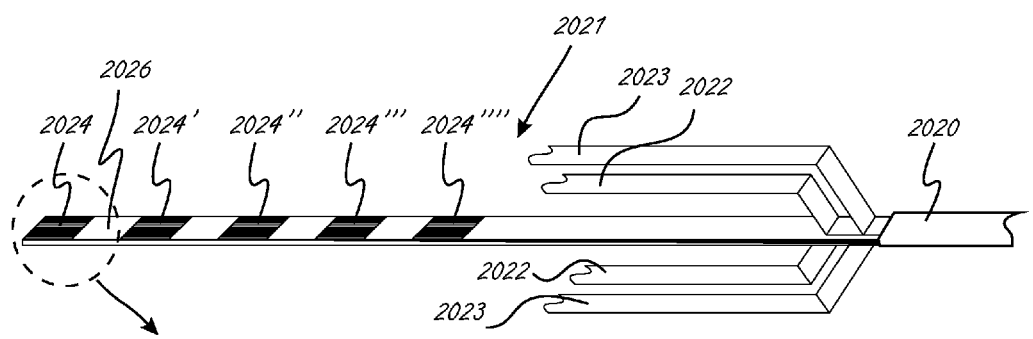
FIG. 19A illustrates a portion of an exemplary medical tool that includes a flexible circuit strip.
Figure 19B:
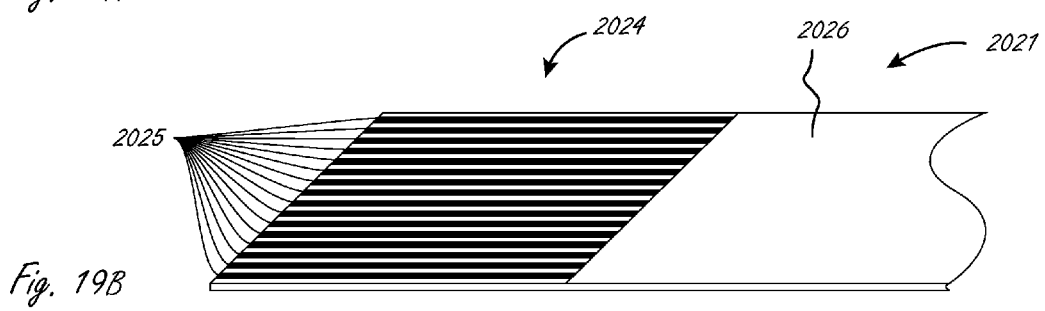
FIG. 19B illustrates an exemplary proximal portion of a strip.

FIGS. 19A and 19B illustrate an exemplary conductor strip (also referred to herein as a flexible circuit strip) 2021 that can be included in any of the conductor bundles herein. The embodiment in FIGS. 19A and 19B is an example of a conductor strip that can be included in bundle 2020 from FIGS. 17 and 18. The embodiment in FIGS. 19A and 19B can be incorporated into any other system herein.

Figure 19C:
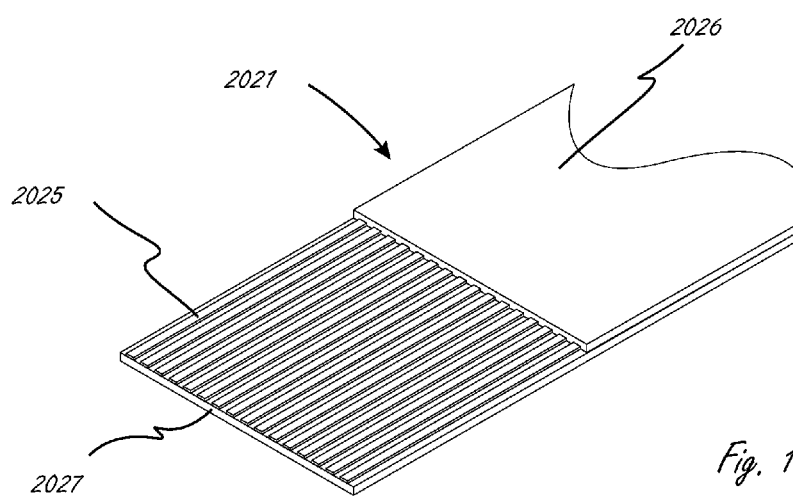
FIG. 19C illustrates a detailed view of an exemplary proximal portion of a strip.
Figures 19D, 19E, 19F, 19G:
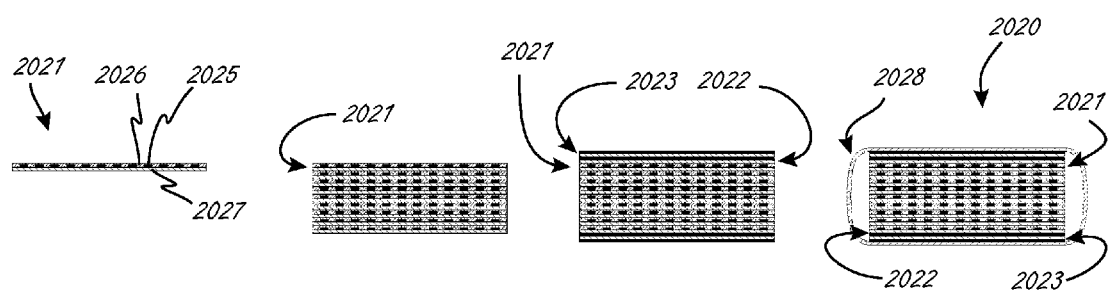
FIG. 19D illustrates an end view of an exemplary flex strip.
FIG. 19E illustrates an exemplary stack of flex strips.
FIG. 19F illustrates an exemplary stack of flex strips and ground and shield strips.
FIG. 19G illustrates an exemplary bundle including a tubing material around a stack of strips and shield and ground strips.

As shown in FIGS. 19A, 19B and 19G, conductor bundle 2020 comprises a plurality of flex circuit strips, including multi-trace strips 2021, as well as conductive strips for grounding 2022 and shielding 2023 (only a portion of which are shown). Each multi-trace strip comprises a plurality of conductive traces 2025, which can be seen clearly in FIGS. 19B, 19C and 19D. The number traces 2025 in FIGS. 19D-19G is twelve, and the number of traces in FIGS. 19A-19C is sixteen, and they are both exemplary as to the number of traces 2025 that can be used. Each strip 2021 can be approximately 0.072" wide and 0.0022" thick, and can optionally comprise sixteen 0.0022" wide×about 0.0007" thick conductive (e.g., copper) traces, each spaced approximately 0.0022" apart. The traces are disposed on an insulating substrate layer 2027, such as a polyimide substrate, and the traces can be at least partly covered by a cover layer 2026, such as a photoimageable film cover ("PIC") layer or other dry film solder mask (DFSM) or other similar material. The cover layer generally extends along most of the bundle, except at discrete locations in proximal and distal regions for electrical coupling. In other embodiments, the strip 2021 is approximately 0.055" wide and comprises twelve conductive traces (see FIGS. 19D-19G). In other embodiments, the strip 2021 is approximately 0.037" wide and comprises eight copper conductive traces. The outer strips 2022 and 2023 used for grounding and shielding may have a similar construction and dimension except they can comprise a single full width strip of copper. As optimized for a 2D piezo array, a stack of approximately seven 16-trace strips 2021 would be required (or nine 12-trace, or fourteen 8-trace), along with one each of strips 2022 and 2023 on each side of the stack of multi-trace strips. FIG. 19E illustrates a portion of an exemplary bundle 2020 with nine strips 2021 stacked together. FIG. 19F illustrates a portion of the bundle that includes nine strips 2021 stacked, as well as ground strip 2022 and shield strip 2023 (only those on top are labeled). The complete bundle may optionally be held together with a, for example without limitation, about 0.001" wall thickness shrink tube, such as the tubing 2028 in FIG. 19G. The flex circuit dimensions and number of traces discussed above are for a particular configuration of a piezo-electric array (and/or an ASIC controller thereof) and may be varied depending on how the number and size of array elements are optimized for the particular application.

The proximal end of each flex circuit strip has the conductive material (e.g., gold-plated copper) exposed over a length of approximately, for example, 3 mm through removal of the cover layer 2026 at location 2024. Location 2024, and other exposed locations described herein, is generally referred to as a "contact." It is understood that when used in this context, the contact actually includes a plurality of separated conductive traces (such as shown in region location), each of which is adapted to be in electrical communication with its own corresponding conductive element. "Contact" is therefore not limited to mean only a single electrical connection between two conductive elements. While FIG. 19A shows a plurality of exposed regions 2024, the embodiment in FIG. 19A will first be described herein as if there is only one exposed region (i.e., region 2024 at the proximal end). The strip 2021 can be made to create an electrical connection to matching exposed contacts 2031, shown in FIGS. 20A-C, for conductive traces on the PCB 2030. In some embodiments, sixteen individual traces, sized and spaced to match sixteen traces in the multi-trace strip 2021, would be provided within a given contact 2031. An ACF (anisotropic conductive film), soldering, conductive adhesive, mechanical connection, or any combination of these may be used to achieve a suitable electrical connection (electrical coupling) between the strip traces and the PCB contacts.

Figure 20A:
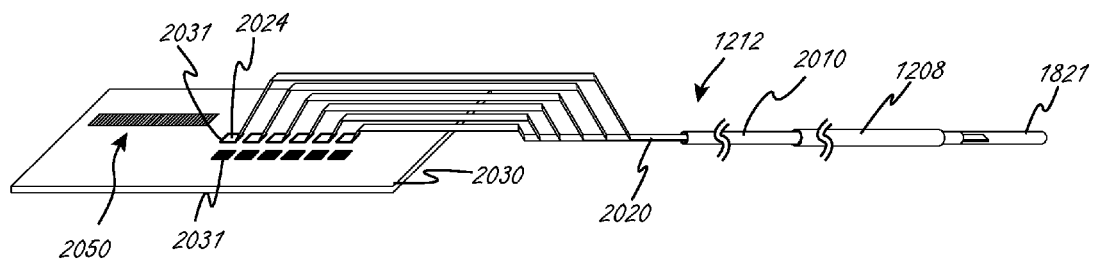
FIGS. 20A and 20B illustrate an embodiment in which a plurality of flex circuit strips have a staggered length and exposed locations are attached to a PCB at contacts provided in a similarly staggered length.
Figure 20B:
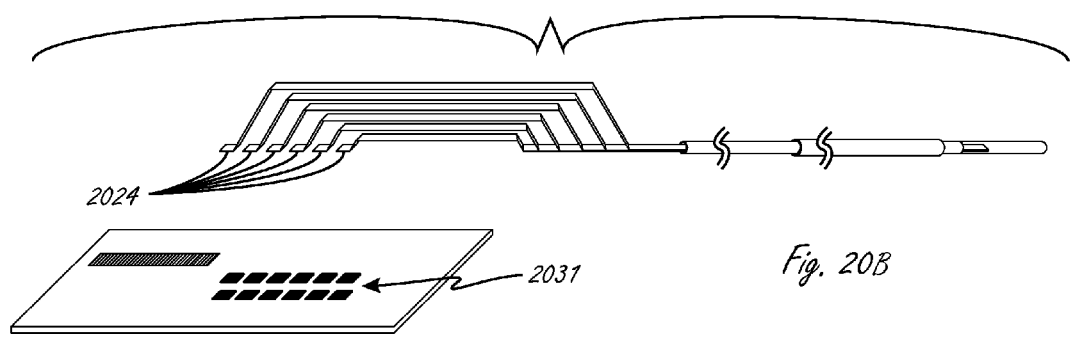

As illustrated in FIG. 20A and FIG. 20B, the plurality of flex circuit strips (not all are illustrated) preferably have a staggered length such that the exposed locations 2024 (each strip has an exposed location 2024 at its proximal end) are attached to the PCB 2030 at contacts 2031 provided in a similarly staggered length. One or more of an array (preferably a linear array) of contacts 2031 could all be on one side of the PCB, or a second array (or array plurality) 2031' (see FIG. 20B) could be provided on the underside of the PCB. Those on the other side of the PCB could allow exposed regions 2024 of other strips to be attached to the other side of the PCB, creating more room and connection options.

Figure 20C:
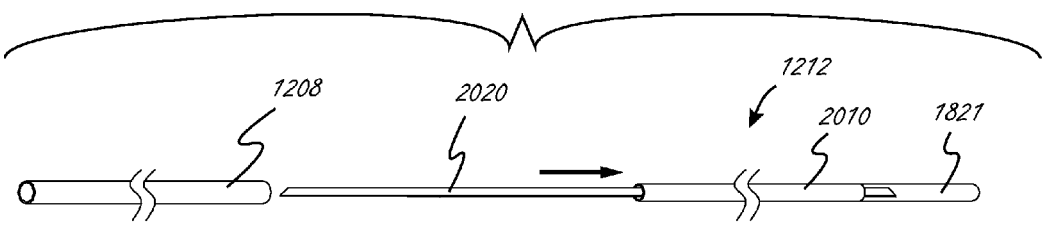
FIG. 20C illustrates an exemplary method of moving a tool distally and out of a sheath, optionally a steerable sheath.

As part of any of the reposing processes described herein, the strip-to-PCB connection may be disconnected to allow the entire tool portion 1212, which includes the now disconnected conductor bundle 2020 (disconnected from the PCB), to be slideably removed out of the distal end of the sheath portion 1208, as illustrated in the direction of the arrow shown in FIG. 20C. Once removed, the outside of the tool portion 1212 and at least the inner and outer surfaces of the sheath portion 1208 may be cleaned and decontaminated. The tool portion 1212 may then be back-loaded proximally through the sheath portion 1208 until the distal working end 1821 is properly seated in relation to the distal end of sheath portion 1208, as is described in more detail herein. The proximal ends of strips 2021, 2022, and 2023 are then reattached to the exposed contacts 2031 and 2031', which can be the same contacts or different contacts. In the case of ACF bonding, the same ACF material may be used and/or it may be cleaned and new ACF material applied prior to bonding. The connection integrity and ultrasound performance may then be tested to verify acceptable performance. This reposing process can be used on any of the systems herein.

One aspect of the disclosure herein is a method of disassembling a system that has already been exposed to a bodily fluid of a subject (e.g., exposed to a blood environment, an esophagus, etc.), the system including a medical tool such as an ultrasound probe, a steerable shaft, and a handle assembly. The method can include providing a handle assembly, a steerable sheath that has been exposed to a bodily fluid environment of a subject, and an ultrasound probe that has been exposed to the bodily fluid environment of the subject, the handle assembly in operable communication with the steerable sheath and the ultrasound probe, the handle assembly including a handle body with an outer surface that can be gripped by a user, a first actuator adapted to be moved relative to the handle body, and a second actuator adapted to be moved relative to the handle body, the steerable sheath having a distal deflectable region that is in operable communication with at least one pull wire, wherein the first actuator is in operable communication with the pull wire such that actuation of the first actuator relative to the handle body causes deflection of the distal deflectable region, and wherein the second actuator is adapted to be rotated relative to the handle body and is also adapted to be moved axially relative to the handle body, and wherein the second actuator is in operable communication with the ultrasound probe such that axial movement of the second actuator relative to the handle body causes axial movement of the ultrasound probe relative to the distal end of the steerable sheath, and such that rotation of the second actuator relative to the handle body causes rotation of the ultrasound probe relative to the distal end of the steerable sheath, the ultrasound probe having a distal portion that includes an ultrasound transducer, the distal portion extending further distally than a distal end of the steerable sheath and having an outer dimension greater than a dimension of a lumen of the steerable sheath in which the probe is disposed, the ultrasound probe further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the second insulation layer defining a probe contact, the probe contact electrically coupled to an electrical contact on a printed circuit board, where the printed circuit board or any of the printed circuit boards herein can be a flexible circuit board. An exemplary system that could be used in this method is shown in FIGS. 11A and 11B. The "providing" step above (or in any other method herein) simply requires that the system be available for the following method steps, and does not require an act of providing or giving the system to another person or entity. Thus, a system simply sitting on a tabletop has been "provided" in this context.

The method of disassembly further includes electrically disconnecting the probe contact from the electrical contact on the printed circuit board, which is described herein.

The method of disassembly further optionally includes moving the ultrasound probe distally relative to the steerable sheath and out of the distal end of the steerable sheath, such as is illustrated in FIG. 20C.

The method of disassembly can optionally further include, but does not necessarily need to include, cleaning at least a portion of the ultrasound probe, the portion comprising a region of the ultrasound probe that was, before the moving step, not extending out of the sheath, and optionally disposed within the handle assembly. For example, in FIGS. 11A and 11B, a portion of the medical device is disposed within the handle assembly.

The method of disassembly can optionally further include, but does not necessarily need to include, at some time after the optional cleaning step, electrically coupling the probe contact to either the printed circuit board or a different printed circuit board.

The method of disassembly can further comprise (and may in fact require), at some time before the moving step, releasing the ultrasound probe from a releasably secured engagement with a handle assembly component. In some embodiments the ultrasound probe will not be able to be removed from the handle assembly without first doing this.

Releasing the ultrasound probe from a releasably secured engagement with a handle assembly component can comprise releasing the probe from a releasably secured engagement with a handle assembly component that is in direct or indirect operable communication with the second actuator. For example, FIG. 11A illustrates a medical device releasably secured to handle assembly component 1755, which in that embodiment is described as a tool lock. A method of disassembly can include, prior to the moving step, releasing the ultrasound probe from a releasably secured engagement with tool lock 1755, which is in this embodiment is also an example of a handle assembly component that is in direct or indirect operable communication with second actuator 1780.

In some embodiments herein, an ultrasound probe and handle assembly are adapted so that the probe can be moved axially (distally and proximally) relative to the sheath. Bodily fluids such as blood can enter into the space between the probe and sheath, thus necessitating cleaning before reuse of the usually relatively expensive probe. In some embodiments, the distal tip of the ultrasound probe has a larger outermost dimension than the distal end of the steerable sheath. This can be desirable as a way of minimizing the footprint of the sheath within a patient. After the probe has been used and exposed to a bodily fluid, the probe thus cannot be retracted proximally within and relative to the sheath to disassemble the probe from the sheath. The probe must then be removed distally relative to and from the sheath in order to repurpose the probe. Because the probe is attached at its proximal end to some type of connector (e.g., directly or indirectly to an ultrasound console), the probe must therefore first be taken out of electrical communication with the connector prior to moving the probe distally relative to the sheath.

In an alternate embodiment, during a reposing process it may be more efficient and/or reliable to not re-attach the original exposed locations 2024 of the conductive strips 2021 (and, if necessary, 2022 and 2023). In this case, as illustrated in FIGS. 19A and 19B, each strip 2021 may be provided with a plurality of exposed locations 2024, 2024', 2024", etc. (each optionally about 3 mm in length) staggered in a distal direction along the strip length. Thus, the original location 2024, as well as a section of layer 2026, may be trimmed off or removed using other techniques, and the next most proximal location 2024' can be used for the new connection attachment. This process can also be repeated for future reposing processes until all of the exposed locations are used. This would also serve to limit the number of reuses of the device. The exposed but not-in-use locations on the strips can also be protected until ready for use with a, for example, peel-away insulating low tack adhesive strip. In other embodiments, this protective layer could be a paste, an adhesive, or a cured polymer having sufficient dielectric properties and conformability to insulate adjacent exposed conductors within a given strip. The material is preferably reversibly adhered such that it can be easily peeled or dissolved away from the exposed conductors without damaging the conductors. In some embodiments a covering layer that is disposed over the traces can be ablated away (e.g., using a laser, sandblasted, or sanded) to reveal an exposed region of traces, which can then be used as a contact location.

In some embodiments alternative to that shown in FIGS. 19A and 19B, the strip can first be attached with the only exposed region being proximal-most region 2024, and wherein the cover layer 2026 extends distally without any discontinuities in layer 2026. After a first use, region 2024 can be removed. To expose another conductive region, a portion of the now-proximal end of layer 2026 can be removed, such as by ablation, or if the layer 2026 is a peel-away section, peeling it away. This process can be repeated as needed after each use to create new exposed conductive regions.

Figure 21:
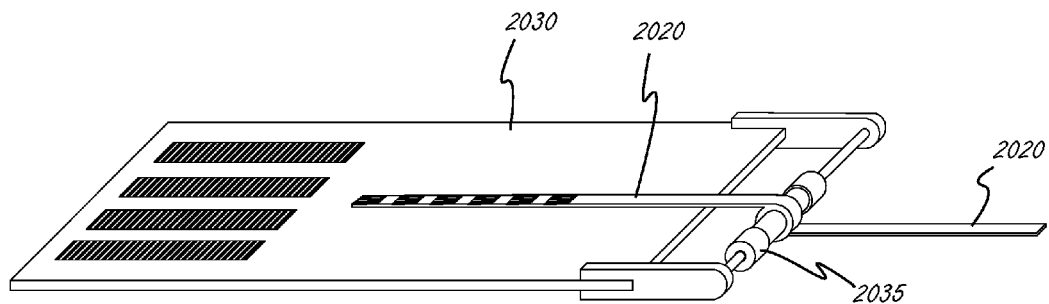
FIG. 21 illustrates an exemplary embodiment in which a conductor bundle can be reversibly spooled or wrapped around a spool comprising a rod, tube, spindle or similar rotatable structure.

In embodiments in which the flex circuit strips are trimmed or removed using any suitable technique to attach the next exposed element of the flex circuit strips to the PCB, it may be necessary to advance the strips forward to establish the electrical connection. This may be difficult or impossible if the strips are confined and immovable within a tube, or otherwise securely housed, up to the PCB. As illustrated in the exemplary embodiment in FIG. 21, to allow extra length to be advanced relative to the tube, a conductor bundle 2020 (which can be the same as bundles 2020 herein or different bundles) could be reversibly spooled or wrapped around a spool 2035 comprising a rod, tube, spindle or similar rotatable structure, for a length suitable to advance out all exposed elements. Before winding, the conductor bundle could be first passed through a slot passing transversely through the central axis, or the bundle could be wound from one end of the outer surface of the spool to the other. Thus after trimming off one contact set, the conductors are unwound off the spool to make the next set of connections on the PCB 2030. The spool preferably has a central axis which could be mounted on the distal end of the PCB or within a mechanism just distal to the board, and secured within the proximal connector 2015. The spool may also serve to protect the connections to the PCB from being strained due to tensile or twisting forces applied to the flex conductor bundle. To prevent premature unwinding, the spool could be fitted with a keyed feature reversibly connected to the PCB or other location within the proximal connector or connector housing itself.

If removing the original connection to the PCB at connectors 2031 compromises the integrity of these connections, the PCB could include a plurality of arrays of redundant connectors 2031', 2031," etc. to which connections can be made with each reposing cycle of the device.

In another embodiment, the PCB could simply be replaced with a new identical PCB to which the exposed ends 2024 (or 2024', etc.) of the flex circuit strips could be attached.

Figure 22:
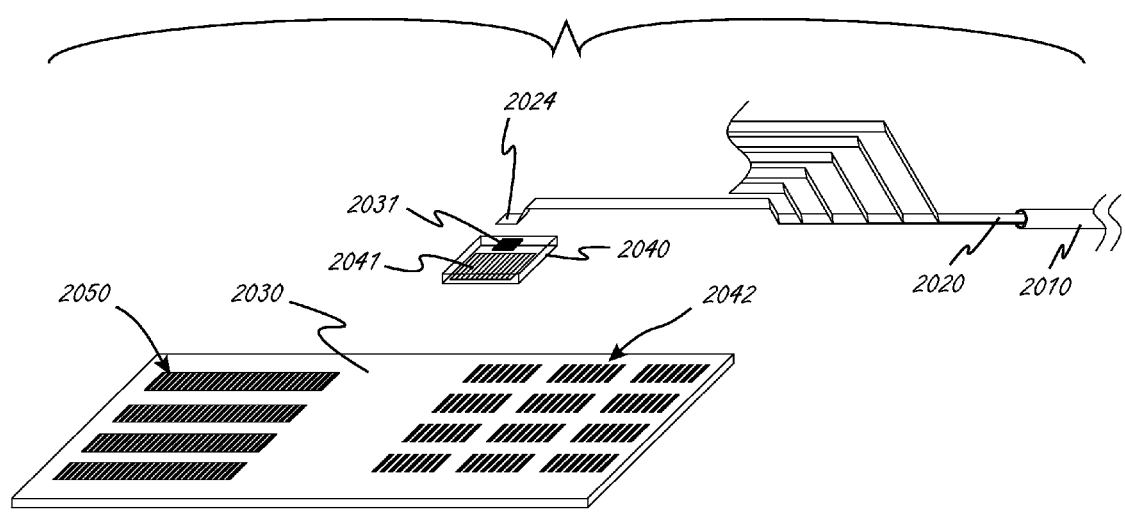
FIG. 22 illustrates a portion of an exemplary embodiment in which exposed flex circuit ends are attached to a disposable mini-PCB element which has a same size connection on one side, but a larger exposed connection on the opposite side.

FIG. 22 illustrates another embodiment in which exposed flex circuit ends (2024 or 2024') could be attached to a disposable mini-PCB element 2040, which has the same connection 2031 on one side, but larger exposed connections 2041 on the opposite side, linked through traces in the mini-PCB, suitable for a reusable mechanical connection to the PCB 2030. The mechanical connection from connections 2041 on the mini-PCB 2040 is made against matching exposed mechanical connections 2042 on the PCB 2030. Spring clips or other suitable holding mechanisms could be integrated into the PCB to hold the mini-PCB contacts against those on the PCB. Each individual trace from each contact 2042 is linked to individual exposed contacts 2050 on another portion, preferably more proximal, of the PCB. The individual PCB traces may also pass through other useful circuitry on the PCB. The exposed contacts 2050 are configured for a mechanical mating for electrical conduction to similar contacts 2060 on a mating connector cable (e.g., cable 2070) which links the medical tool to the console. During the reposing process, the mini-PCB may be unclipped from the PCB and the flex circuit detached or clipped away from (as previously described) the mini-PCB.

After removal, cleaning, and reassembly of the tool in the sheath, the flex circuits may then be reattached to new mini-PCBs that are re-connected to the original PCB.

To allow access to the PCB 2030, and spool 2035 if applicable, the proximal connector (e.g., proximal connector 2015) can be fitted with a removable housing that has a custom design for it to mate with other portions of the connector and/or the PCB 2030 and/or the spool 2035. Optionally, to remove this housing completely will require breaking the housing thereby rendering it non-functional, requiring replacement prior to continued use.

Distal to the spool, the conductor bundle 2020 is optionally irreversibly secured within the tool outer member 2010. The tool outer member 2010 preferably also extends proximal to the handle 1206. After disconnection of the flex circuit from the PCB, to allow the assembly of the tool outer member 2010 and conductor bundle to be removed from the handle 1206 and sheath portion 1208, the assembly is preferably slideable within any tubular connection line between the handle 1206 and proximal connector 2015. Reversible seals, similar to those previously described herein, could also be used between the tool outer member 2010 and tubular connection line.

The construction of the medical tool 1212 may be optimized to minimize the diameter and to provide optimal torque response of the distal working end (e.g., working end 1812). In some embodiments, the flex circuits are routed through an inner lumen of tool member 2010, similar to that illustrated in FIG. 16B.

FIG. 23 illustrates the cross-section of the bundled stack 2020 inside member 2010. In this embodiment, the ~0.072" width of the flex circuit bundle is optimized for the width of the ASIC to which the piezoelectric components are mounted. Taking into account shrink tubing around the stack, the stack dimensions are approximately 0.028" thick× 0.085" wide. The inner lumen of the tool member 2010 would require an inner dimension, in at least one dimension, of approximately 0.089". This dimension then drives the outer dimension of the member 2010 which also impacts the inner and outer dimensions of the sheath portion 1208.

While the conductor bundle 2020 may simply be routed through a circular inner lumen of the tool member 2010 as shown in FIG. 23, it may alternatively be constrained within a non-circular lumen such as is illustrated in FIG. 24. In this configuration, additional "D" lumens are also provided such that additional stiffening members 2100 may be added to create a more uniform bending stiffness in a variety of directions such that the stiffness along the long axis of the conductor bundle 2020 does not dominate the shaft stiffness. This will serve to minimize "whipping", or sudden jerks in torque response, as the tool member 2010 is torqued.

FIG. 25 illustrates an embodiment, similar to that shown in FIG. 24, where different size lumens are provided to accept stiffening members 2101 and 2102. These may also serve to create a uniform bending stiffness. The tool member 2010 is preferably constructed with an outer braid of wire and/or fiber which is heat laminated with a jacket of thermoplastic polymer (e.g., Pebax in durometers ranging 25 D to 72 D or other suitable catheter material known in the art).

The embodiment of FIG. 26 illustrates a "D" shaped member 2103 applied to either side of the flex circuit bundle 2020. This creates a uniformly round member which can be held in place with a thin wall (~0.001" thick) heat shrink tube. In one embodiment, the assembly may then be inserted into a tool member shaft 2010. In another embodiment, the tool member shaft can be constructed directly around the conductor bundle. For example, to improve torque response and minimize the size of the tool 1212, multiple fibers and/or metal wire (round or ribbon shaped) may be braided directly over the conductor bundle 2020. A jacket of polymer (such as Pebax in a range of durometers from 25 D-72 D, or other common catheter materials) may be laminated with heat to reflow the polymer over the entire braid to form a uniform member. A polymer layer similar to the jacket may also be laminated over the conductor bundle before braiding to improve the reflow penetration of the polymer into the braid during heat lamination.

For the embodiments of FIGS. 23-26, the luminal space between the conductor bundle and inner diameter of shaft 2010 could be used to route pull wires used to steer the tool 1212 independent of the steerable sheath 1202. The stiffeners themselves could be used as pull wires, or replaced with more traditional pull wires (e.g., round and/or flattened stainless steel or nitinol, or a cable braid of these materials). The pull wires could be fixed at the distal end of the shaft 2010 and actuated in a manner similar to other embodiments described herein.

In an alternative embodiment, illustrated in FIG. 27 and showing exemplary bundle 2020, each flex circuit strip could be made with approximately half the number of traces, and thus have approximately half the width (~0.037" wide). For the specific embodiment described above, this requires doubling the number of multi-trace circuits to approximately 14. This, in combination with the ground and shielding flex circuits, creates as stack of about 17 flex circuits. The resulting width and height are more even, close to 0.042" each with the heat shrink. This allows a more efficient use of space within the lumen of member 2010 and improves the uniformity of the torque response. As described for FIG. 26, the stack could be inserted into a tubular shaft or the shaft constructed around it with a braid and jacket. Other configurations are also contemplated between those illustrated in FIG. 23 and FIG. 27 for optimization with the transducer assembly. For instance, the width of the flex bundle with heat shrink may be limited to approximately 0.068" with a stack of 13 flex circuits being approximately 0.031" thick.

In another embodiment, the ground and/or shield strips are replaced by separate braids or winds of conductor wire (individually insulated or not insulated) around the bundle of flex multi-trace flex circuits. If the ground and shield conductors are not insulated, an insulating polymer layer may be added between the braids of ground and shielding conductors. This conductor braid may be provided in addition to or instead of the braid of fibers and/or metal wire/ribbon. Insulated conductors may also be woven into a braid of fibers and/or metal wire/ribbon to optimize torque response of tool 1212 and minimize the number of braided layers.

In another embodiment, the conductor bundle 2010 may be twisted to provide a more balanced cross-section along the majority of the length of the tool 1212. The conductor bundle may be run straight in the distal few centimeters to facilitate connection to the distal working end 1821.

In another embodiment, the individual flex circuit strips may be wrapped around the outer dimension of an elongated central core member. The core may be a solid or tubular construction of a polymer or metal, or a composite braid. The wraps may be a group of parallel strips in one layer, but may be wrapped in multiple layers. Preferably, layers are wrapped in alternating directions to optimize torque of the unit. The wrapped strips are preferably laminated against the central core with a polymer jacket. In other embodiments the inside of the jacket may have a loose clearance with the conductor strips to allow some flexural movement for strain relief of the strips. A braid over this jacket followed by lamination of a second jacket over the braid may also be provided. Similar to the embodiment described above, the ground and/or shield conductors may be replaced with braided or wound conductors.

As used herein, "cleaning" can refer to any type of cleaning, such as without limitation: cleaning an interior of an outer shaft using a flushing system of cleaner and/or disinfectant and optionally mechanical scrubbing with small brushes; mechanical cleaning (e.g., wipes, brushes) an outer portion of an outer shaft and/or outer portion of a medical device shaft (e.g., ultrasound probe) with a cleaner/disinfectant, and optionally submerging the shaft in an ultrasound bath of cleaner/disinfectant for a specified period of time. "Cleaning" as used here does not refer to a specific cleaning process, but rather refers to the general idea of cleaning an object.

Regardless of the reference number with which they are labeled, any of the handle assemblies, medical tools, steerable sheaths, and electrical connections herein can be used together in a system in any combination with each other.

Any of the technology, including ultrasound and steering technology, in any of the following U.S. patent references may be incorporated into any of the medical tools, devices, systems, or methods of use thereof herein, the disclosures of which are incorporated by reference herein: U.S. Pat. Nos. 6,100,626, 6,537,217, 6,559,389, 7,257,051, 7,297,118, 7,331,927, 7,338,450, 7,451,650, 7,451,650, 7,527,591, 7,527,592, 7,569,015, 7,621,028, 7,731,516, 7,740,584, 7,766,833, 7,783,339, 7,791,252, 7,791,252, 7,819,802, 7,824,335, 7,966,058, 8,057,397, 8,096,951, 8,207,652, 8,207,652, 8,213,693, 8,364,242, 8,428,690, 8,451,155, 8,527,032, 8,659,212, 8,721,553, 8,727,993, 8,742,646, 8,742,646, 8,776,335, 8,790,262, 8,933,613, 8,978,216, 8,989,842, 9,055,883, 9,439,625, 9,575,165, 9,639,056, and 20080287783.

What is claimed is:

1. A method of disassembling a system exposed to a bodily fluid of a subject, the system including an ultrasound probe, a steerable shaft, and a handle assembly, comprising:
providing a handle assembly, a steerable sheath that has been exposed to a bodily fluid environment of a subject, and an ultrasound probe that has been exposed to the bodily fluid environment of the subject, the handle assembly in operable communication with the steerable sheath and the ultrasound probe, the handle assembly including a handle body with an outer surface that can be gripped by a user, a first actuator adapted to be moved relative to the handle body, and a second actuator adapted to be moved relative to the handle body, the steerable sheath having a distal deflectable region that is in operable communication with at least one pull wire, wherein the first actuator is in operable communication with the pull wire such that actuation of the first actuator relative to the handle body causes deflection of the distal deflectable region, and wherein the second actuator is adapted to be rotated relative to the handle body and is also adapted to be moved axially relative to the handle body, and wherein the second actuator is in operable communication with the ultrasound probe such that axial movement of the second actuator relative to the handle body causes axial movement of the ultrasound probe relative to the distal end of the steerable sheath, and such that rotation of the second actuator relative to the handle body causes rotation of the ultrasound probe relative to the distal end of the steerable sheath,
the ultrasound probe having a distal portion that includes an ultrasound transducer, the distal portion extending further distally than a distal end of the steerable sheath and having an outer dimension greater than a dimension of a lumen of the steerable sheath in which the probe is disposed, the ultrasound probe further including a flexible circuit strip, the flexible circuit strip comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the insulation member defining a probe contact, the probe contact electrically coupled to an electrical contact on a printed circuit board of the system;
electrically disconnecting the probe contact from the electrical contact on the printed circuit board of the system;
moving the ultrasound probe distally relative to the steerable sheath and out of the distal end of the steerable sheath;
cleaning at least a portion of the ultrasound probe, the portion comprising a region of the ultrasound probe that, prior to the moving step, does not extend outside of the steerable shaft and optionally comprises a region that, prior to the moving step, was disposed within the handle assembly; and
after the cleaning step, electrically coupling the probe contact to either the printed circuit board of the system or a different printed circuit board.

2. The method of claim 1, wherein the ultrasound probe comprises a plurality of flexible circuit strips, each of the plurality of flexible circuit strips comprising an insulating substrate, a plurality of conductive traces disposed on and extending along the insulating substrate, a portion of each of the plurality of conductive traces covered by an insulation member, and a portion of the plurality of conductive traces not covered by the insulation member, the portion of the plurality of conductive traces that are not covered by the insulation member defining a probe contact.

3. The method of claim 1, further comprising, before the moving step, releasing the ultrasound probe from a releasably secured engagement with a handle assembly component.

4. The method of claim 3, wherein releasing the ultrasound probe from the releasably secured engagement with the handle assembly component comprises releasing the probe from the releasably secured engagement with the handle assembly component that is in direct or indirect operable communication with the second actuator.

* * * * *